United States Patent
Klein et al.

(10) Patent No.: US 7,820,696 B2
(45) Date of Patent: *Oct. 26, 2010

(54) COMPOUNDS AND METHODS FOR CONTROLLING FUNGI, BACTERIA AND INSECTS

(75) Inventors: Richard B. Klein, Cary, NC (US); Jeffrey L. Selph, Cary, NC (US); John J. Partridge, Chapel Hill, NC (US); John Reinhard, Raleigh, NC (US)

(73) Assignee: Mycosol, Inc., Cary, NC (US)

( * ) Notice: Subject to any disclaimer, the term of this patent is extended or adjusted under 35 U.S.C. 154(b) by 474 days.

This patent is subject to a terminal disclaimer.

(21) Appl. No.: 11/745,111

(22) Filed: May 7, 2007

(65) Prior Publication Data

US 2007/0213299 A1     Sep. 13, 2007

Related U.S. Application Data

(62) Division of application No. 10/792,496, filed on Mar. 3, 2004, now Pat. No. 7,220,761.

(60) Provisional application No. 60/480,995, filed on Jun. 23, 2003, provisional application No. 60/524,775, filed on Nov. 25, 2003, provisional application No. 60/525,075, filed on Nov. 25, 2003, provisional application No. 60/524,784, filed on Nov. 25, 2003, provisional application No. 60/450,599, filed on Mar. 3, 2003.

(51) Int. Cl.
C07D 401/02    (2006.01)
A01N 43/40    (2006.01)

(52) U.S. Cl. .............. 514/318; 514/343; 514/357; 546/193; 546/276.4; 546/329

(58) Field of Classification Search .................. None
See application file for complete search history.

(56) References Cited

U.S. PATENT DOCUMENTS

| | | | |
|---|---|---|---|
| 3,075,975 A | 1/1963 | Phillips et al. | |
| 3,085,935 A | 4/1963 | Phillips et al. | |
| 3,867,535 A | 2/1975 | Hsieh et al. | |
| 3,883,658 A | 5/1975 | Phillips et al. | |
| 3,920,669 A | 11/1975 | Kristinsson et al. | |
| 3,929,806 A | 12/1975 | Schmid et al. | |
| 3,934,017 A | 1/1976 | Gallay et al. | |
| 3,987,181 A | 10/1976 | Traber et al. | |
| 4,001,254 A | 1/1977 | Schmid et al. | |
| 4,151,298 A | 4/1979 | Drabek et al. | |
| 4,153,723 A | 5/1979 | Drabek et al. | |
| 4,197,307 A | 4/1980 | Gallay et al. | |
| 4,205,077 A | 5/1980 | Aufderhaar et al. | |
| 4,608,379 A | 8/1986 | Boyle | |
| 7,220,761 B2 * | 5/2007 | Klein et al. | ............. 514/318 |

FOREIGN PATENT DOCUMENTS

| | | |
|---|---|---|
| BE | 645532 | 9/1964 |
| EP | 0 513 762 A1 | 11/1992 |
| EP | 1 266 884 A1 | 12/2002 |
| WO | WO 96/29312 A1 | 9/1996 |
| WO | WO 2004/078136 A2 | 9/2004 |

OTHER PUBLICATIONS

West, Anthony R., Solid State Chemistry and its Applications, Wiley, New York, 1988, pp. 358 & 365.*
Baldwin et al., "Rectification and Nonlinear Optical Properties of a Langmuir—Blodgett Monolayer of a Pyridium Dye," *J.Phys.Chem. B*, 06: 12158-12164 (2002).
International Search Report and Written Opinion corresponding to PCT/US2004/006437; Date of Mailing: Oct. 7, 2004.

* cited by examiner

*Primary Examiner*—Zinna N Davis
(74) *Attorney, Agent, or Firm*—Myers Bigel Sibley & Sajovec, PA

(57) ABSTRACT

The present invention includes compounds of pyridinium salts and methods of their use for industrial uses. The present invention also relates to methods of controlling fungi and/or bacteria. The present invention may also be used to control insects.

48 Claims, 27 Drawing Sheets

1

2

3

4

5

6

7

8

60

61

62

1

2

3

4

5

6

7

8

16

17

18

19

20

21

22

23

24

25

33

34

35

36

37

38

39

40

42

36

37

38

39

40

41

42

43

44

COMPOUNDS AND METHODS FOR CONTROLLING FUNGI, BACTERIA AND INSECTS

CROSS REFERENCE TO RELATED APPLICATIONS

This application is a divisional of U.S. patent application Ser. No. 10/792,496, filed Mar. 3, 2004 now U.S. Pat. No. 7,220,761, and claims priority to U.S. Provisional Application No. 60/480,995, filed on Jun. 23, 2003, U.S. Provisional Application No. 60/524,775, filed on Nov. 25, 2003, U.S. Provisional Application No. 60/525,075, filed on Nov. 25, 2003, U.S. Provisional Application No. 60/524,784, filed on Nov. 25, 2003, and U.S. Provisional Application No. 60/450,599, filed on Mar. 3, 2003. The disclosures of each are incorporated herein by reference in their entireties.

FIELD OF THE INVENTION

The present invention generally relates to methods of controlling fungi and/or bacteria. More specifically the present invention relates to controlling fungal or bacterial infestations relating to industrial uses. The present invention may also be used to control insects.

BACKGROUND OF THE INVENTION

Vast demands exist for compounds to control microorganisms in fields other than agriculture. These include the treatment of fabrics to prevent mildew and rot; to inhibit and kill bacterial growth; the treatment of surfaces and substrates to obtain antiseptic conditions for medical, industrial, food processing and household purposes; the treatment of wood for decking or building; the formulation of ink and paints to prevent mold growth and bacterial decomposition; the prevention and treatment of human and animal diseases; and on through an almost infinite spectrum of applications touching our daily lives.

Fungi includes organisms such as slime molds, mushrooms, smuts, rusts, mildews, molds, stinkhorns, puffballs, truffles and yeasts. Fungi are classified in their own kingdom because they absorb food in solution directly through their cell walls and reproduce through spores. Molds are a large group of fungi that are a common trigger for allergies. Molds can exist as tiny particles called "mold spores" present in indoor and outdoor air. There are more than 100,000 species in the world. Molds may grow anywhere they can find moisture sources. Common molds include *Cladosporium, Penicillium, Aspergillus, Alternaria, Fusarium, Stachybotyrs* and *Mucor.*

Mold has been around forever but only recently has it began to support a billion dollar industry of remediation contractors, consultants, laboratories, physicians and attorneys—as evidenced by an explosion of multi-million dollar lawsuits for property damage and personal injury. In Ballard v. Farmers Insurance case, a jury awarded a Texas homeowner $32.1 million, consisting of $6.2 million for remediation or replacement cost of the property damaged as well as living expenses; $12 million in punitive damages; $5 million for emotional distress damages; and $8.9 million in attorneys' fees and costs, for mold damage to the residence. Thus, there is a need to reduce mold in buildings and homes.

There is a continuing need for new antibacterial agents. Although many compounds are known which are useful in the treatment of Gram-positive and Gram-negative bacterial infections as well as other microbial infections, the widespread use of such compounds continues to give rise to resistant strains of microorganisms, i.e., strains of microorganisms against which a particular antibiotic or group of antibiotics, and chemical compositions which was previously effective, is no longer useful. Also, known antibiotics and chemical compositions may be effective against only certain strains of microorganisms or have limited activity against either Gram-positive or Gram-negative, aerobic or anaerobic organisms.

Stilbazium iodide is a known anthelmintic which is reported to be effective against roundworms, threadworms, and whipworms. U.S. Pat. No. 3,075,975 and 3,085,935 recite methods of eradicating infestations of parasitic nematodes inhabiting the intestinal tract.

SUMMARY OF THE PRESENT INVENTION

The present invention relates to methods and compositions comprising stilbazium. One aspect of the present invention is a composition comprising formula (I)

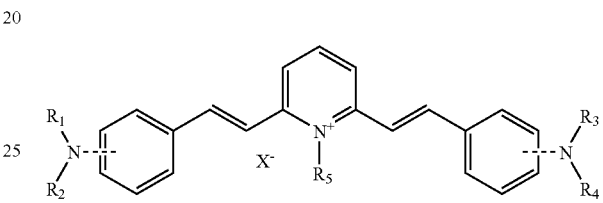

or a solvate thereof wherein said compound is substantially in the E, E configuration The amino moieties may be in either the ortho, meta or para postion. $X^-$ may be an anionic salt, $R_1$, $R_2$, $R_3$, or $R_4$ are independently selected from the group consisting of methyl, ethyl, $C_{1-10}$ alkyl (linear or branched), alkenes (linear or branched), or wherein $R_1$ and $R_2$ or $R_3$ and $R_4$ taken together with the nitrogen atom to which they are attached form pyrrolidino or piperidino rings; and $R_5$ is selected from the group consisting of methyl, ethyl, $C_{1-10}$ alkyl (linear or branched), alkenes (linear or branched), alkynes, n-propyl, i-propyl, n-butyl, i-butyl, substituted and unsubstituted aryl moieties and substituted and unsubstituted benzyl moieties. The substituted and unsubstituted aryl moieties and substituted and unsubstituted benzyl moieties may include, but are not limited to lower alkyl, aryl, benzyl, acyl, amido, amino, alkoxy, carboxy, carboxy ester, alcohol, nitro, trifluoroalkoxy, trifluoroalkyl and halo. $R_5$ may also be an organometallic compound such as organotin, organosilicon, or organogermanium. Additionally, $R_5$ may be $(CH_2)_n\text{-MR}_6$, wherein n is a number from 1 to 6, M is an organometallic compound such as tin, silicon, or germanium, and wherein $R_6$ is a selected from the group consisting of propyl, butyl, or any alkyl compound.

The present invention also relates to methods of controlling fungi and/or bacteria comprising administering a composition comprising any of the below formulas or a solvate thereof.

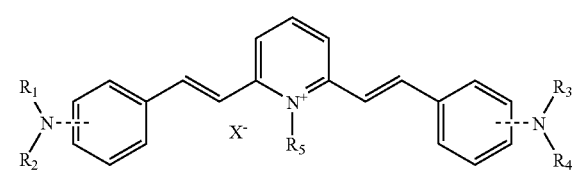

or a solvate thereof, wherein $X^-$ is an anionic salt, wherein $R_1$, $R_2$, $R_3$, or $R_4$ are independently selected from the group consisting of methyl, ethyl, $C_{1-10}$ alkyl, linear or branched, alkenes, or wherein when $R_1$ and $R_2$ or when $R_3$ and $R_4$ are taken together with the nitrogen atom to which they are attached, they form pyrrolidino or piperidino rings. $R_5$ is selected from the group consisting of methyl, ethyl, $C_{1-10}$ alkyl, linear or branched, alkenes, alkynes, n-propyl, i-propyl, n-butyl, i-butyl, substituted and unsubstituted aryl moieties and substituted and unsubstituted benzyl moieties. $R_5$ may also be an organometallic compound such as organotin, organosilicon, or organogermanium. Additionally, $R_5$ may be $(CH_2)_n$-$MR_6$, wherein n is a number from 1 to 6, M is an organometallic compound such as tin, silicon, or germanium, and wherein $R_6$ is a selected from the group consisting of propyl, butyl, or any alkyl compound. The present compound is more commonly known as stilbazium.

The present invention also relates to methods of controlling insects comprising administering a composition comprising any of the above formulas or a solvate thereof.

The present invention also relates to microcapsule compositions that are stabilized against environmental degradation.

DETAILED DESCRIPTION OF THE EMBODIMENTS OF THE INVENTION

Figure 1A:
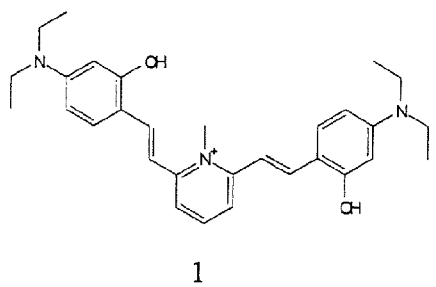
FIGS. 1A-1G show various compounds including a methyl on a pyridine ring at the nitrogen position.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All publications, patent applications, patents and other references cited herein are incorporated by reference in their entireties for the teachings relevant to the sentence and/or paragraph in which the reference is presented.

The present invention relates to pyridinium derivatives, processes for their preparation, methods of their use and compositions comprising such derivatives. Stilbazium iodide is a known anthelmintic which is reported to be effective against roundworms, threadworms, and whipworms. U.S. Pat. Nos. 3,075,975 and 3,085,935 recite methods of eradicating infestations of parasitic nematodes inhabiting the intestinal tract. This compound can be used to control fungi and/or bacteria for industrial uses.

One of the embodiments of the present invention includes a compound comprising:

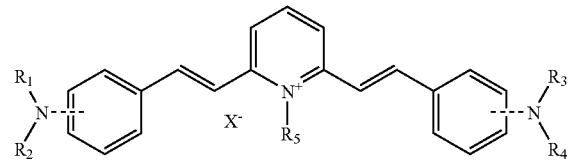

or a solvate thereof, wherein $X^-$ is an anionic salt, wherein $R_1$, $R_2$, $R_3$, or $R_4$ are independently selected from the group consisting of methyl, ethyl, $C_{1-10}$ alkyl (linear or branched), alkenes (linear or branched), or wherein when $R_1$ and $R_2$ or when $R_3$ and $R_4$ are taken together with the nitrogen atom to which they are attached, they form pyrrolidino or piperidino rings. $X^-$ can be selected from the group including fluoride, chloride, bromide, iodide halide, mesylate, tosylate, napthylate, nosylate, para-aminobenzoate, lauryl sulfate, 2,4-dihydroxy benzophenone, 2-(2-hydroxy-5'-methylphenyl)benzotriazole, benzenesulfonate, besylate, ethyl 2-cyano-3,3-diphenyl acrylate and 5-butyl phenyl salicylate. $R_5$ is selected from the group consisting of methyl, ethyl, $C_{1-10}$ alkyl (linear or branched), alkenes (linear or branched), alkynes, n-propyl, i-propyl, n-butyl, i-butyl, substituted and unsubstituted aryl moieties and substituted and unsubstituted benzyl moieties. $R_5$ may also be an organometallic compound such as organotin, organosilicon, or organogermanium. Additionally, $R_5$ may be $(CH_2)_n$-$MR_6$, wherein n is a number from 1 to 6, M is an organometallic compound such as tin, silicon, or germanium, and wherein $R_6$ is a selected from the group consisting of propyl, butyl, or any alkyl compound.

Another embodiment of the present invention includes a compound comprising formula (II)

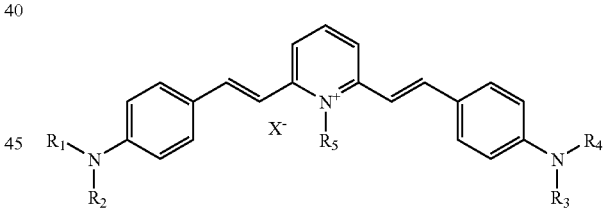

or a solvate thereof, wherein $X^-$ is an anionic salt, wherein $R_1$, $R_2$, $R_3$, or $R_4$ are independently selected from the group consisting of methyl, ethyl, $C_{1-10}$ alkyl (linear or branched), alkenes (linear or branched), or wherein when $R_1$ and $R_2$ or when $R_3$ and $R_4$ are taken together with the nitrogen atom to which they are attached, they form pyrrolidino or piperidino rings. $X^-$ can be selected from the group including fluoride, chloride, bromide, iodide halide, mesylate, tosylate, napthylate, nosylate, para-aminobenzoate, lauryl sulfate, 2,4-dihydroxy benzophenone, 2-(2-hydroxy-5'-methylphenyl)benzotriazole, benzenesulfonate, besylate, ethyl 2-cyano-3,3-diphenyl acrylate and 5-butyl phenyl salicylate. $R_5$ is selected from the group consisting of methyl, ethyl, $C_{1-10}$ alkyl (linear or branched), alkenes (linear or branched), alkynes, n-propyl, i-propyl, n-butyl, i-butyl, substituted and unsubstituted aryl moieties and substituted and unsubstituted benzyl moieties. $R_5$ may also be an organometallic compound such as organotin, organosilicon, or organogermanium. Additionally, $R_5$ may be $(CH_2)_n$-$MR_6$, wherein n is a number from 1 to 6, M is an organometallic compound such as tin, silicon, or germanium, and wherein $R_6$ is a selected from the group consisting of propyl, butyl, or any alkyl compound. The present compound is more commonly known as stilbazium. One of the embodiments of formula I is 2,6,-bis(p-pyrrolidinostyryl)pyridine methiodide.

Alternatively, the $NR_1R_2$ and $NR_3R_4$ moieties may be in various positions as evidenced in the compounds below.

Another embodiment includes Formula III illustrates the $NR_1R_2$ moiety in one meta position.

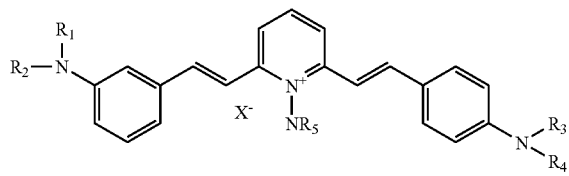

Formula IV illustrates the $NR_1R_2$ and $NR_3R_4$ moieties in both meta positions.

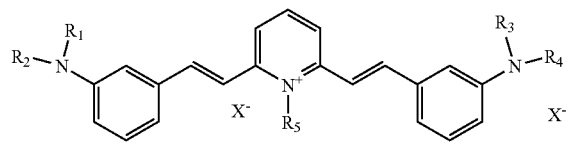

may be an anionic salt, $R_1$, $R_2$, $R_3$, or $R_4$ are independently selected from the group consisting of methyl, ethyl, $C_{1-10}$ alkyl (linear or branched), alkenes (linear or branched), or wherein when $R_1$ and $R_2$ or when $R_3$ and $R_4$ are taken together with the nitrogen atom to which they are attached, they form pyrrolidino or piperidino rings. $R_5$ is selected from the group consisting of methyl, ethyl, $C_{1-10}$ alkyl (linear or branched), alkenes (linear or branched), alkynes, n-propyl, i-propyl, n-butyl, i-butyl, substituted and unsubstituted aryl moieties and substituted and unsubstituted benzyl moieties.

Figure 1A:
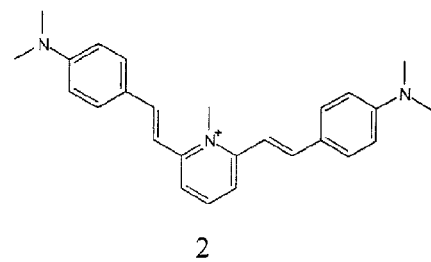
Figure 1A:
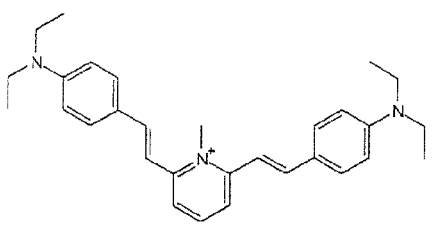
Figure 1A:
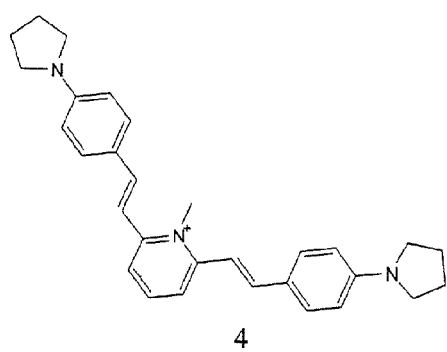
Figure 1A:
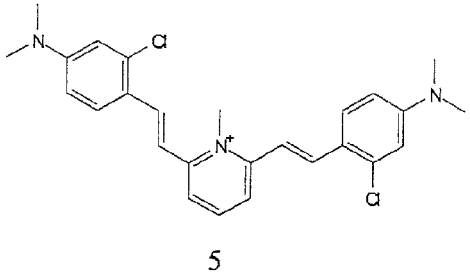
Figure 1A:
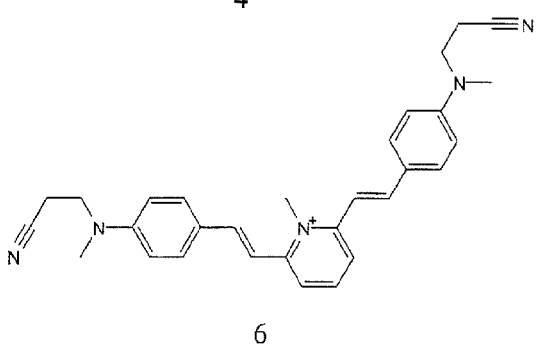
Figure 1A:
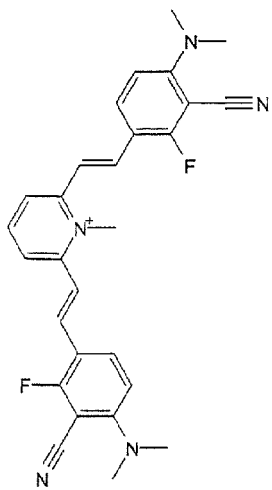
Figure 1A:
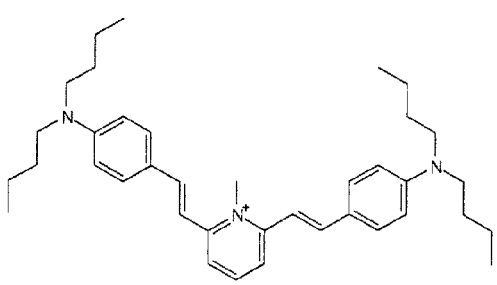
Figure 1B:
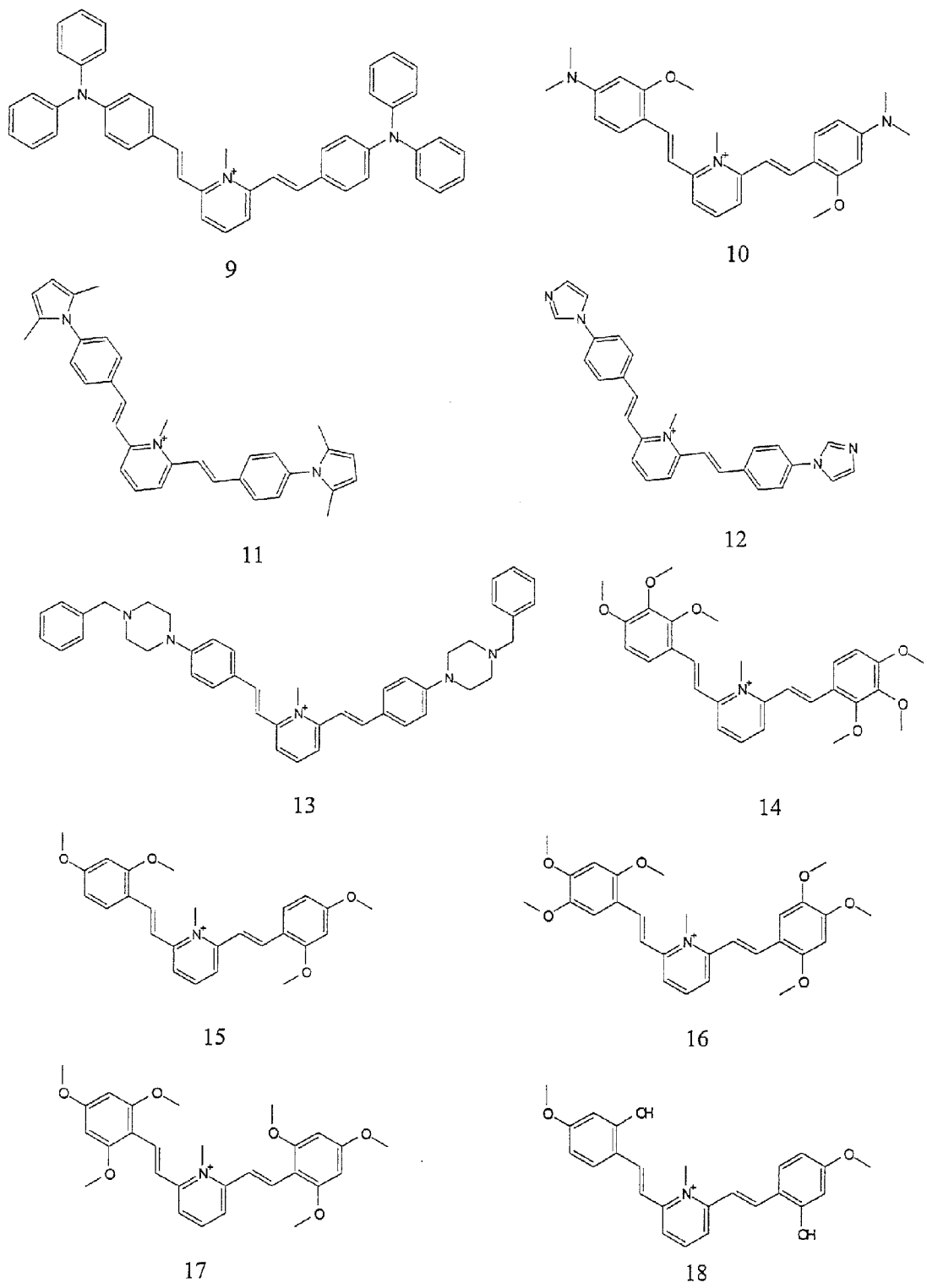
Figure 1C:
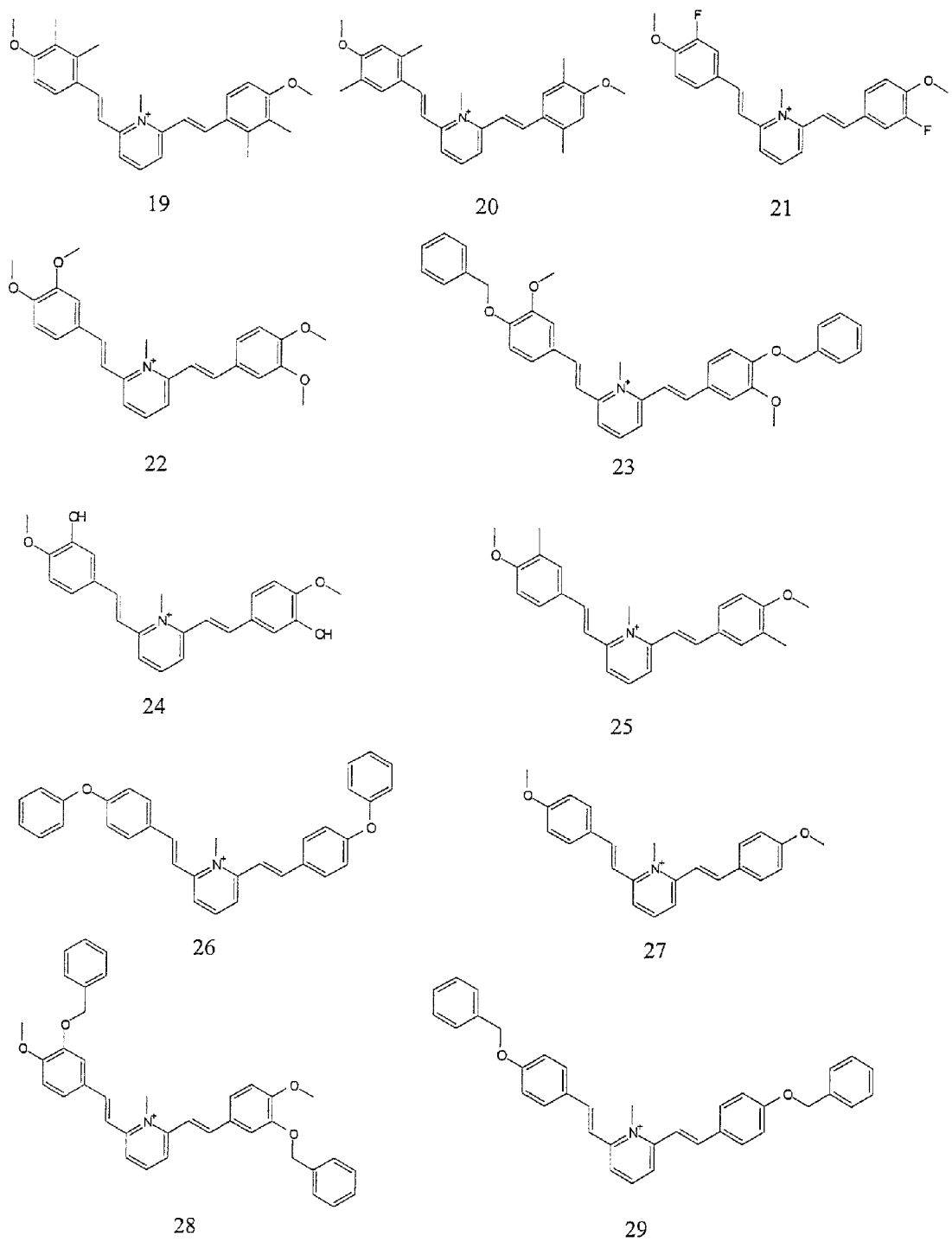
Figure 1D:
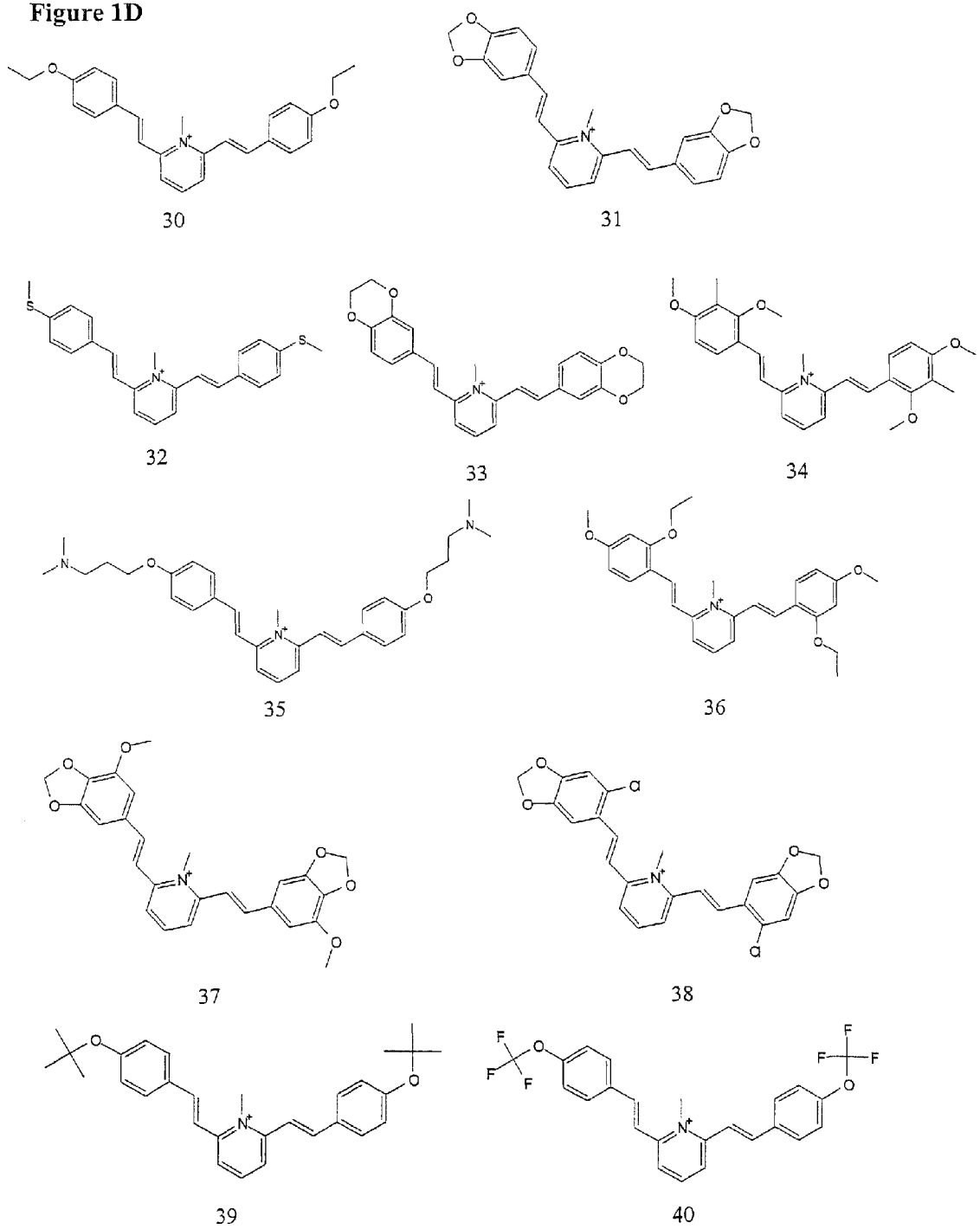
Figure 1E:
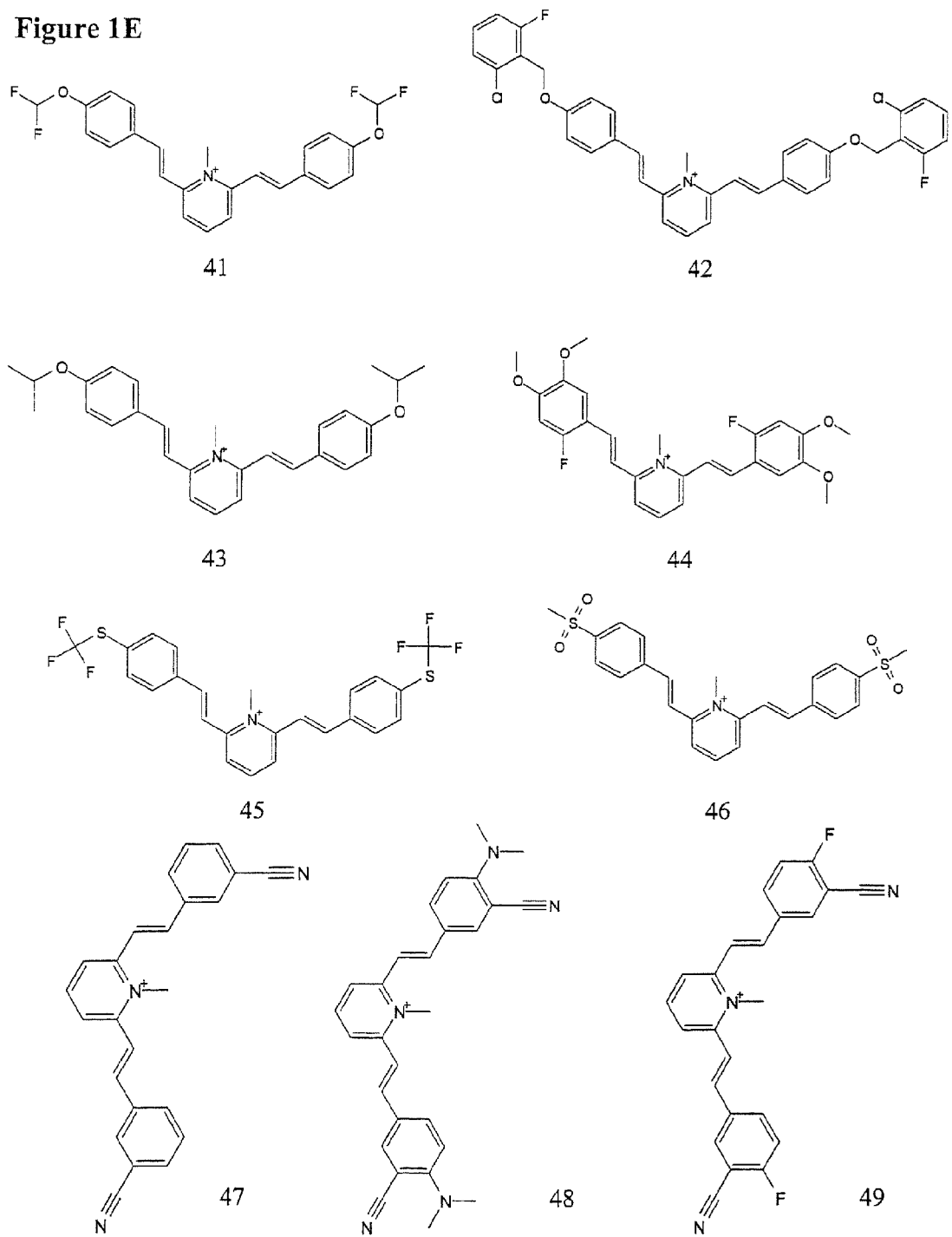
Figure 1F:
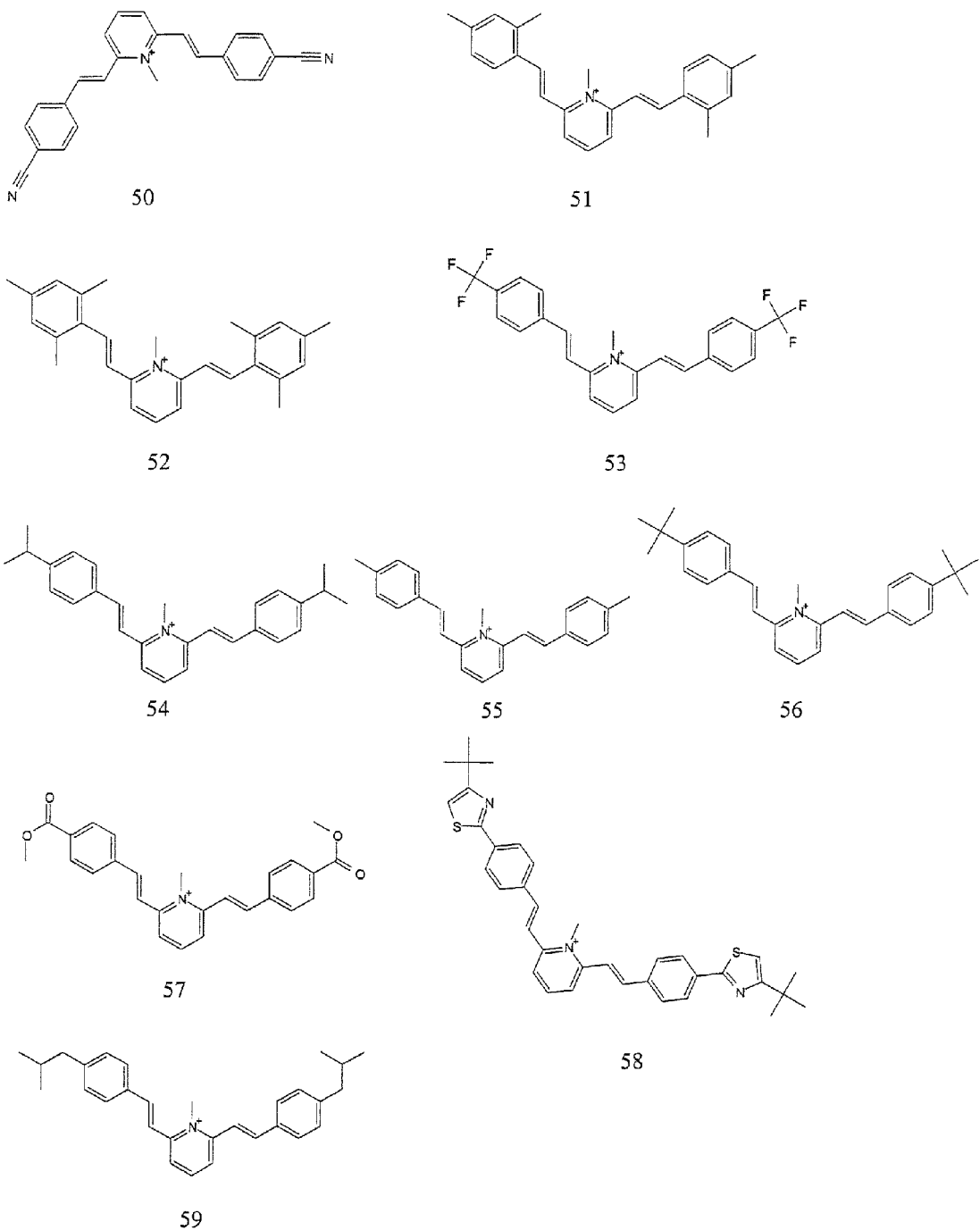
Figure 1G:
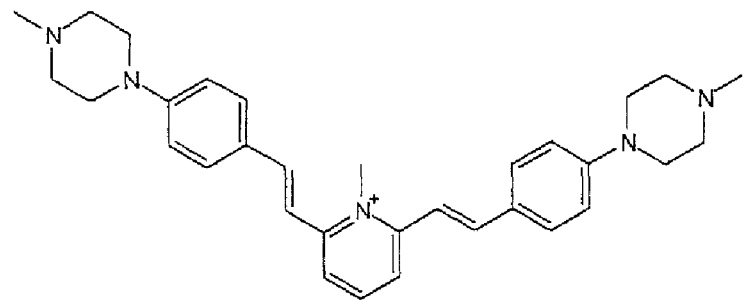
Figure 1G:
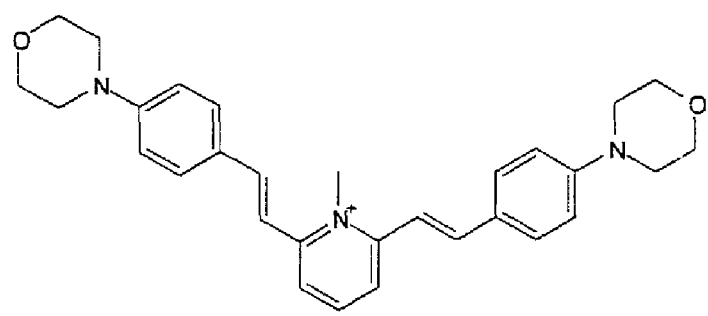
Figure 1G:
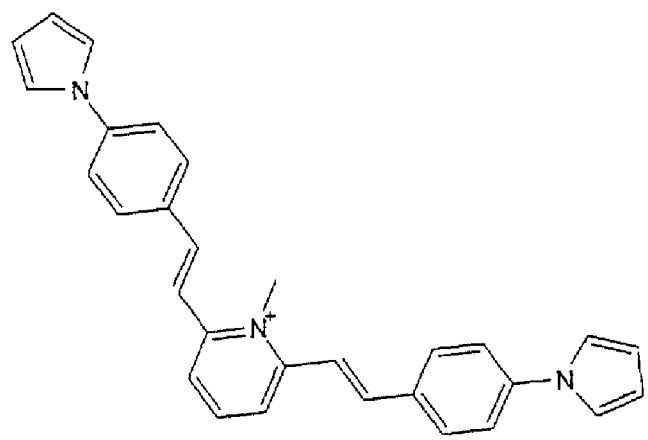
Figure 2A:
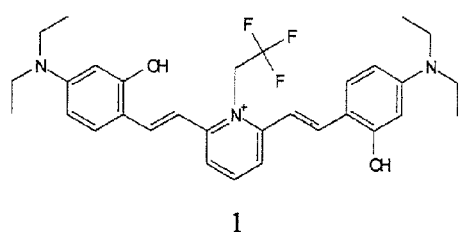
FIGS. 2A-2G depict various compounds including a trifluoroethyl attached to the pyridine ring at the nitrogen position.
Figure 2A:
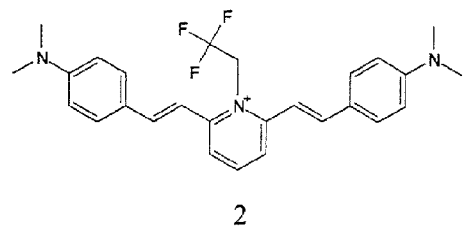
Figure 2A:
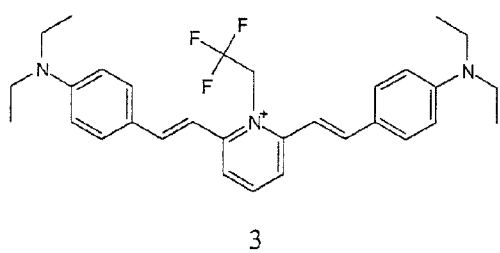
Figure 2A:
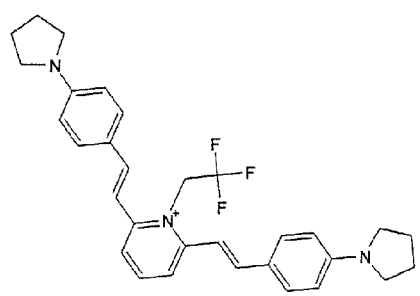
Figure 2A:
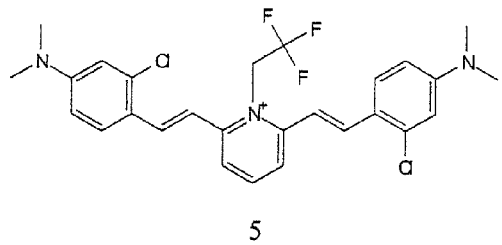
Figure 2A:
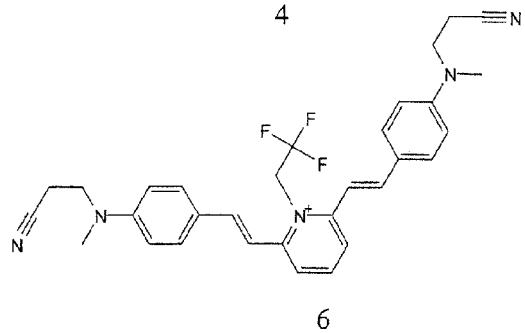
Figure 2A:
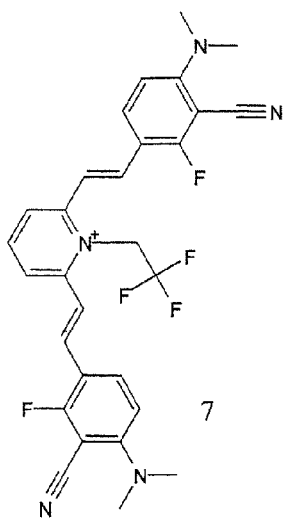
Figure 2A:
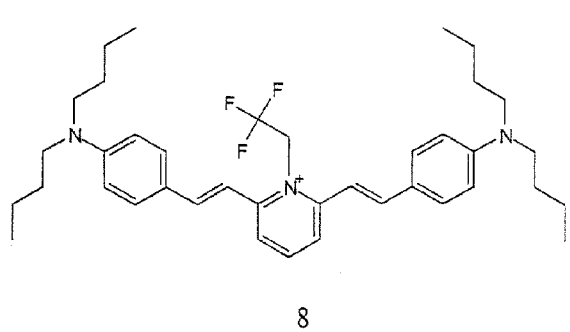
Figure 2B:
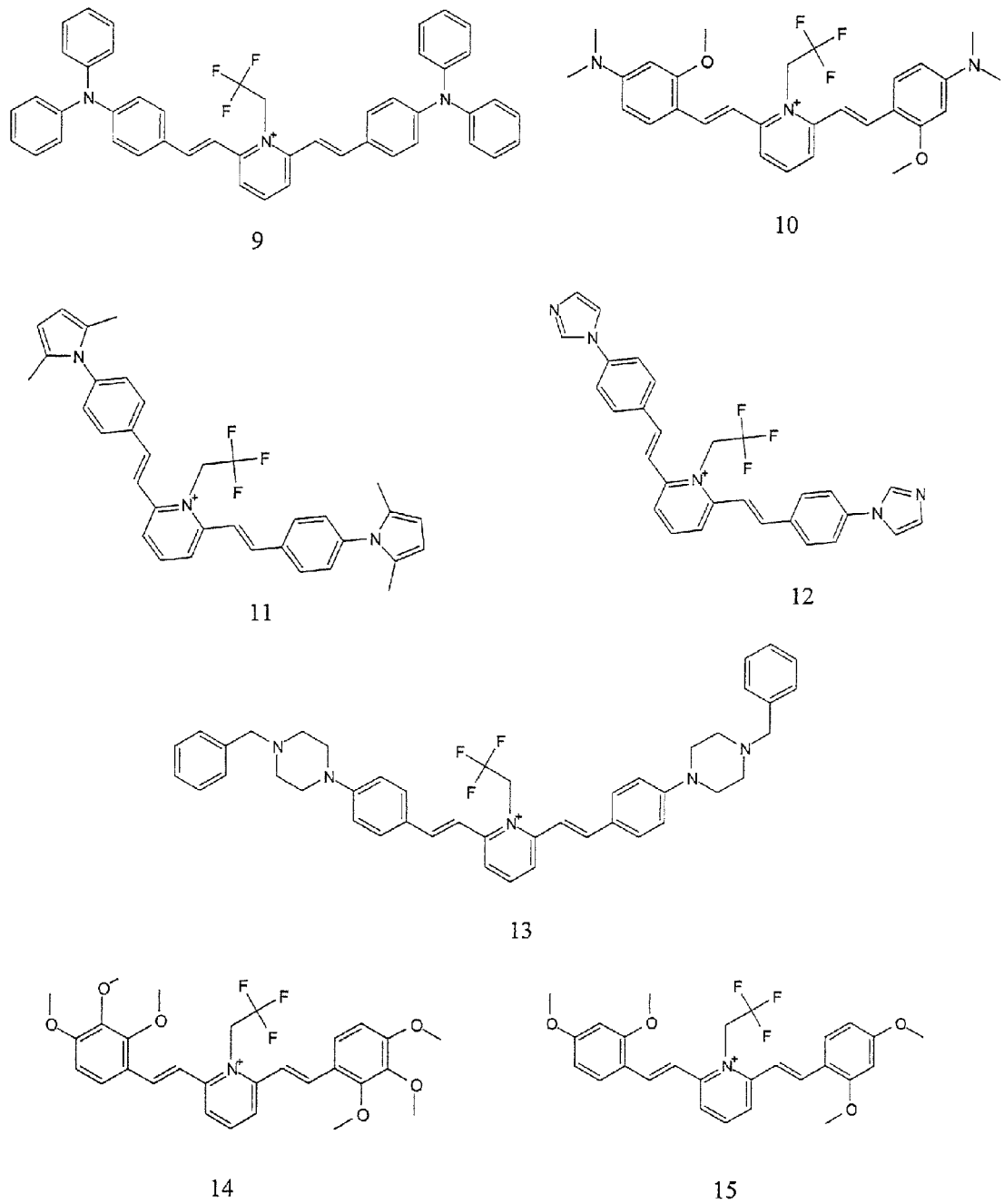
Figure 2C:
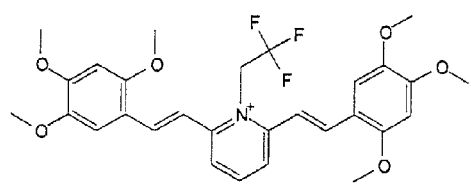
Figure 2C:
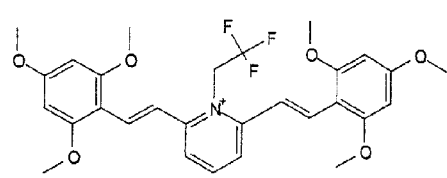
Figure 2C:
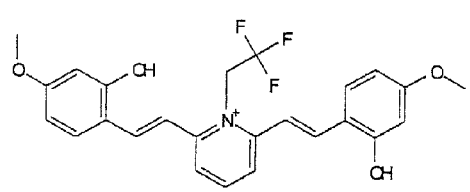
Figure 2C:
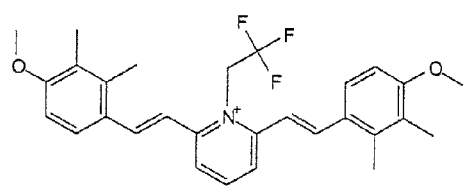
Figure 2C:
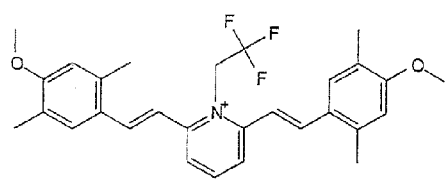
Figure 2C:
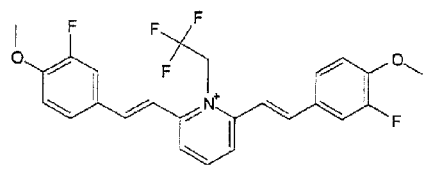
Figure 2C:
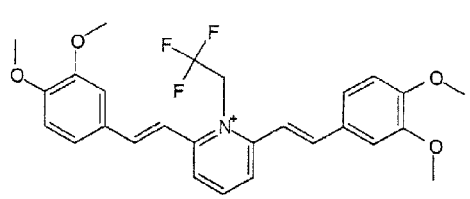
Figure 2C:
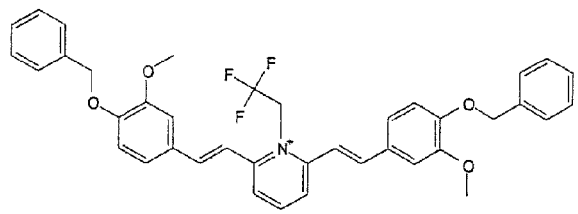
Figure 2C:
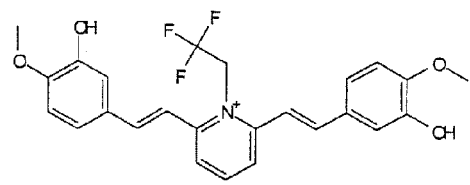
Figure 2C:
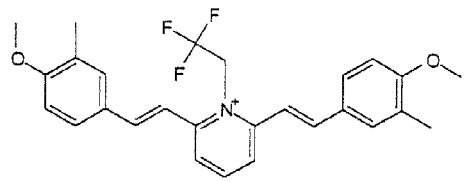
Figure 2D:
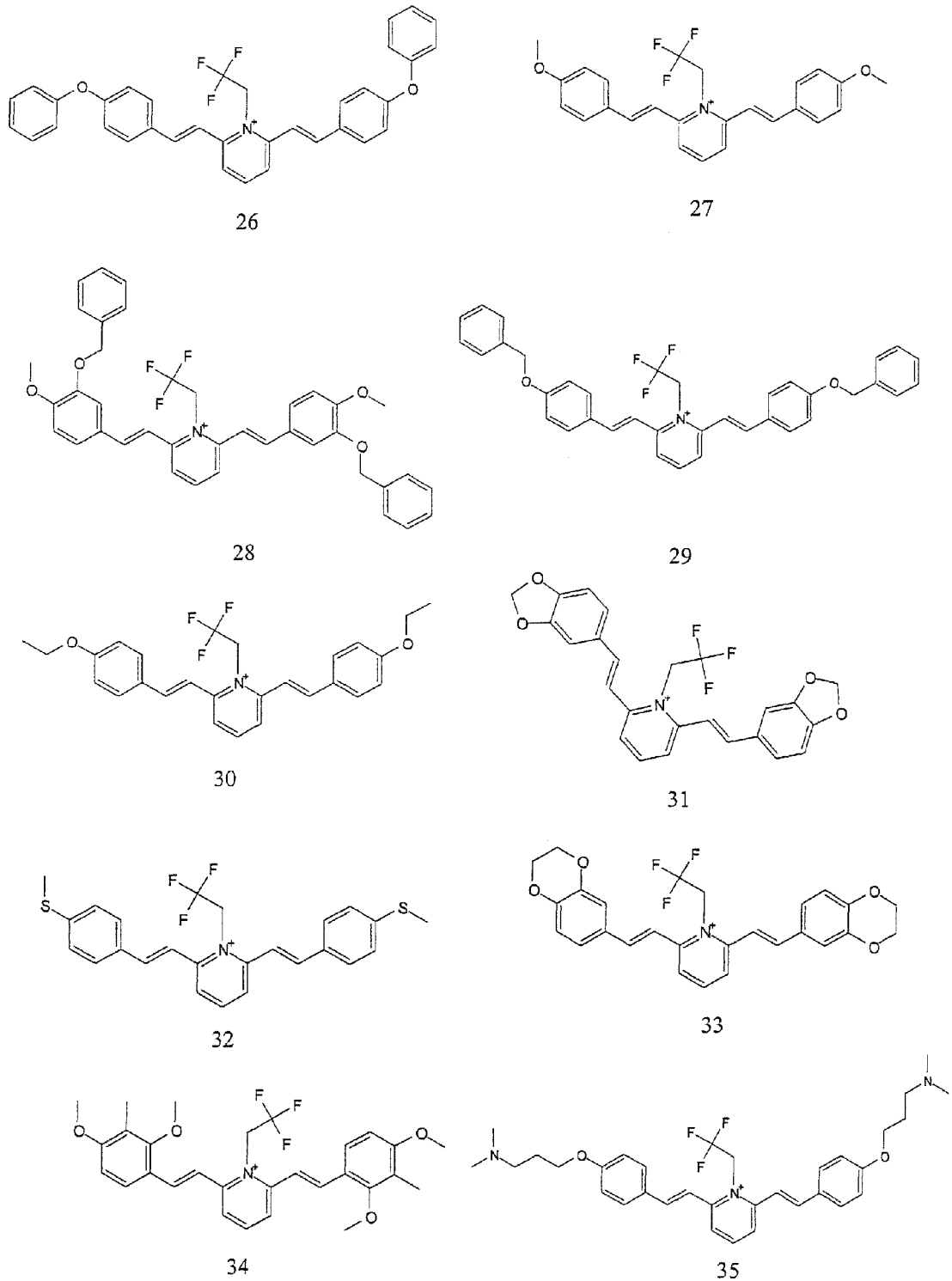
Figure 2E:
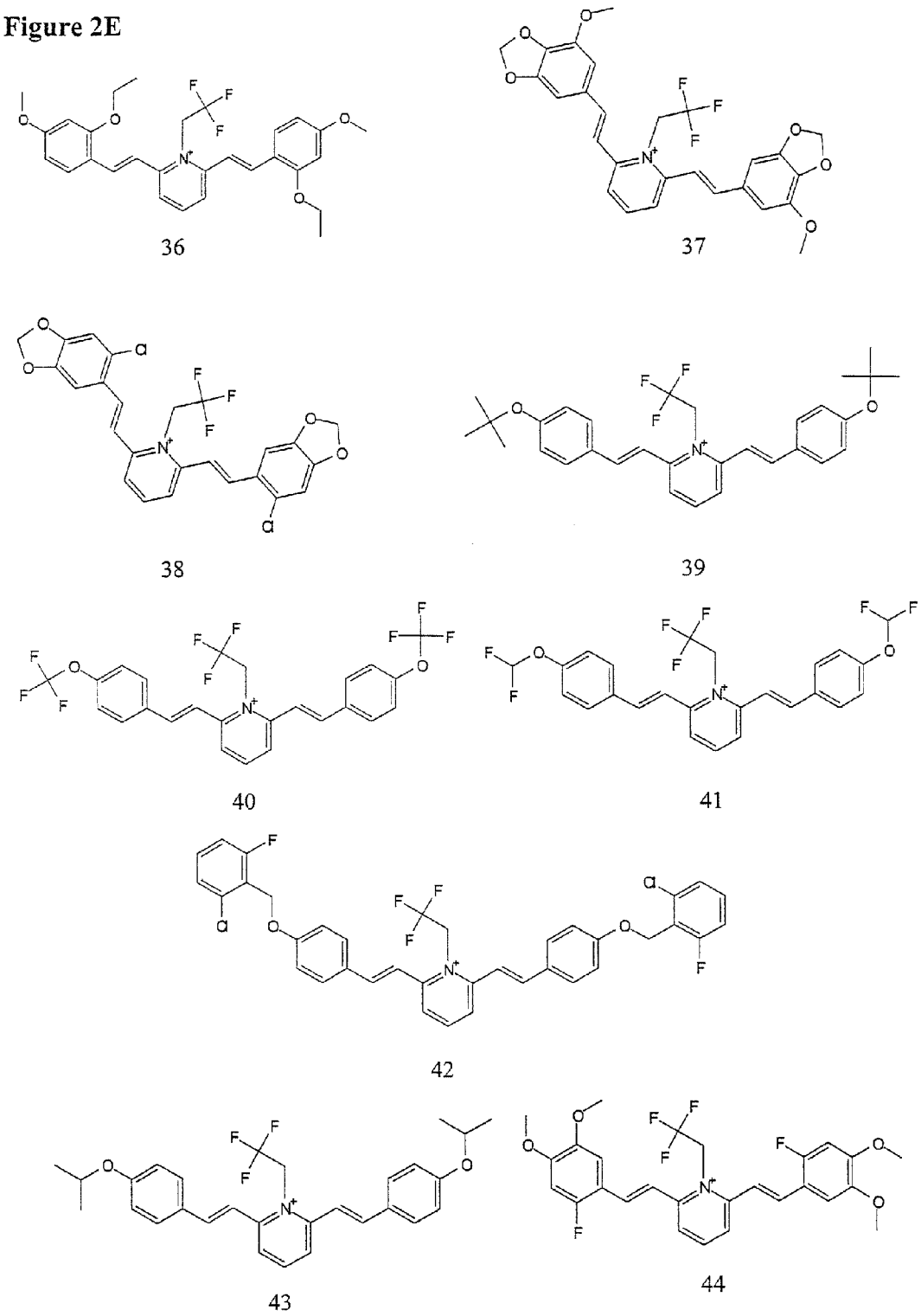
Figure 2F:
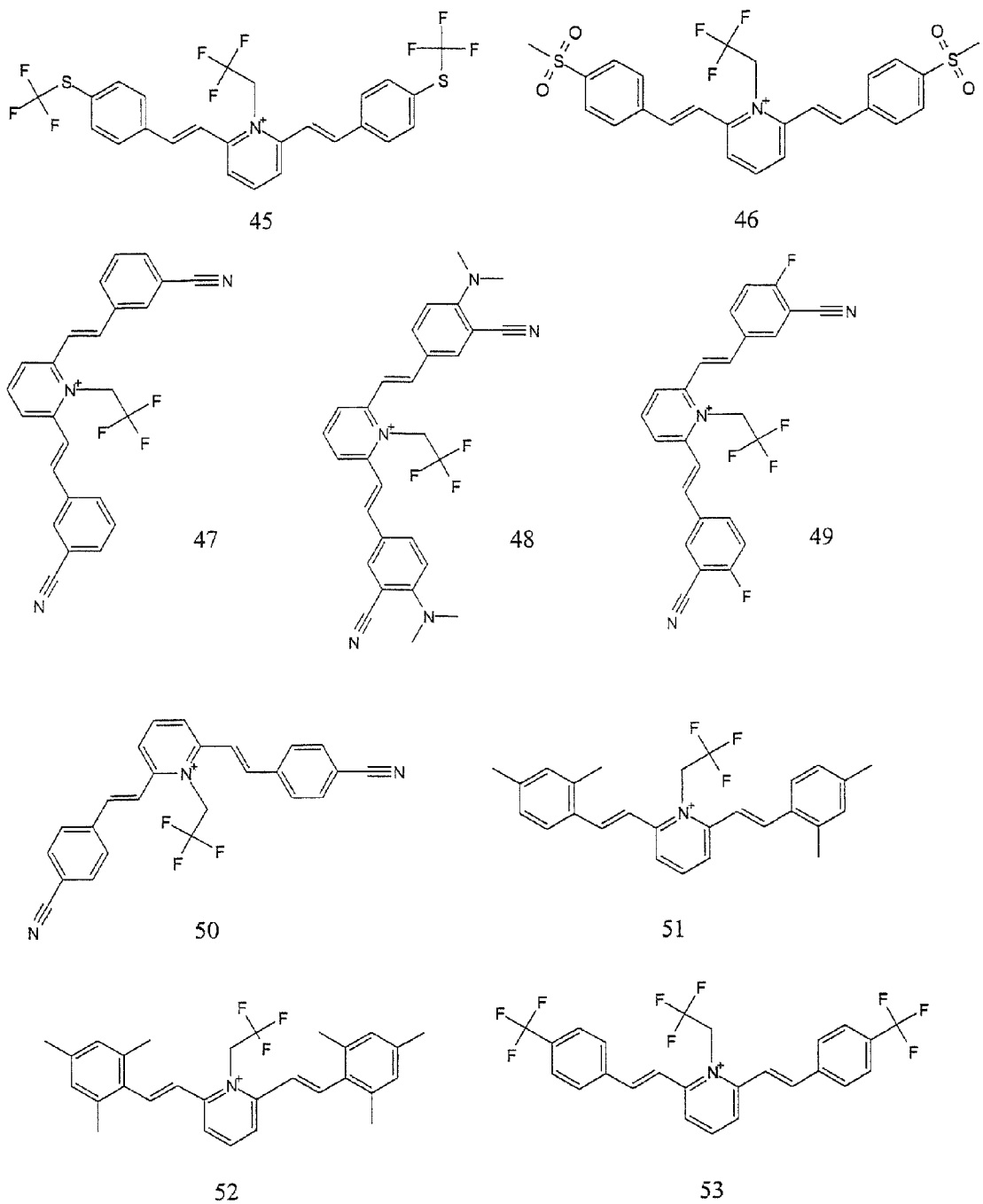
Figure 2G:
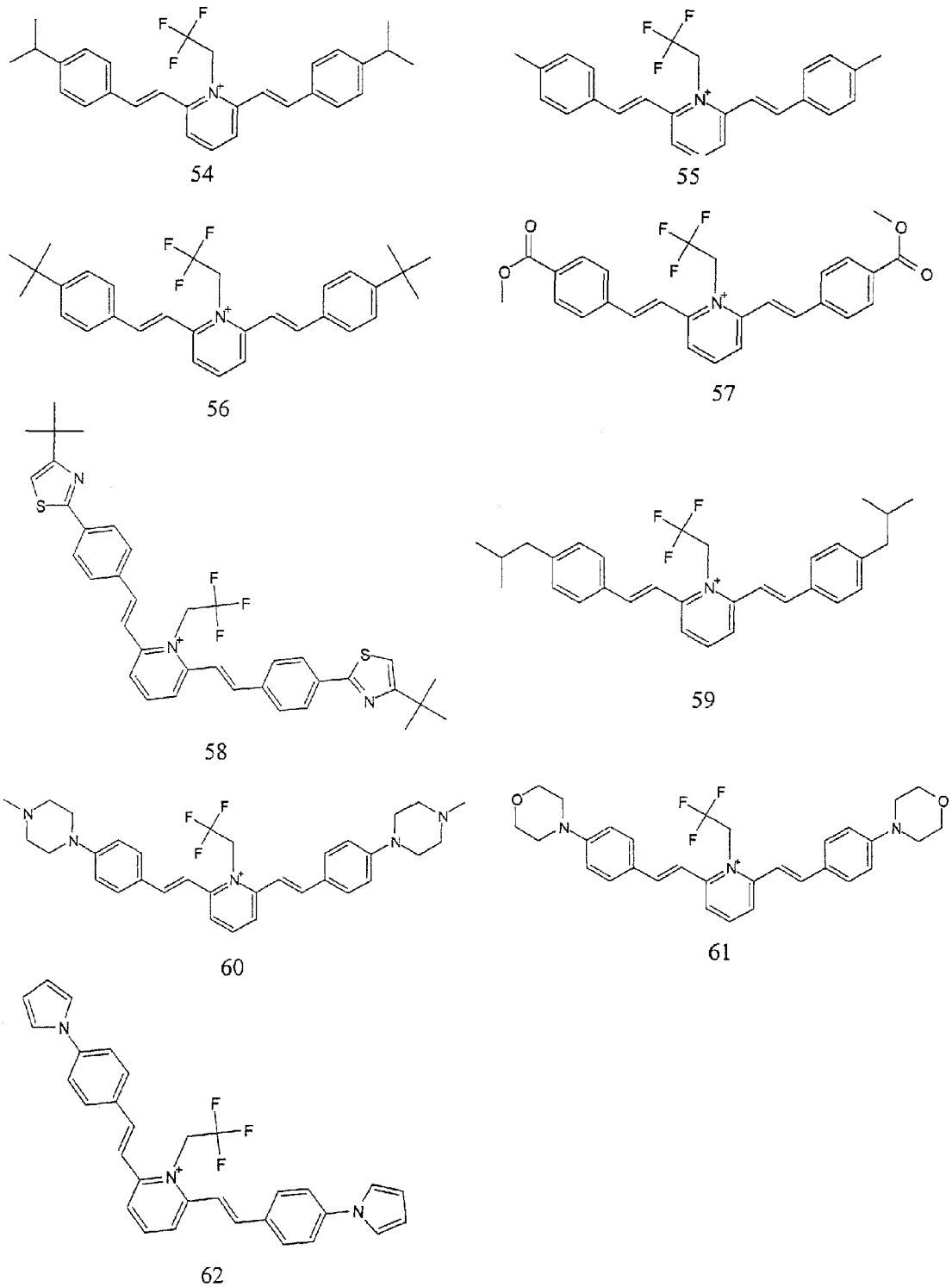
Figure 3A:
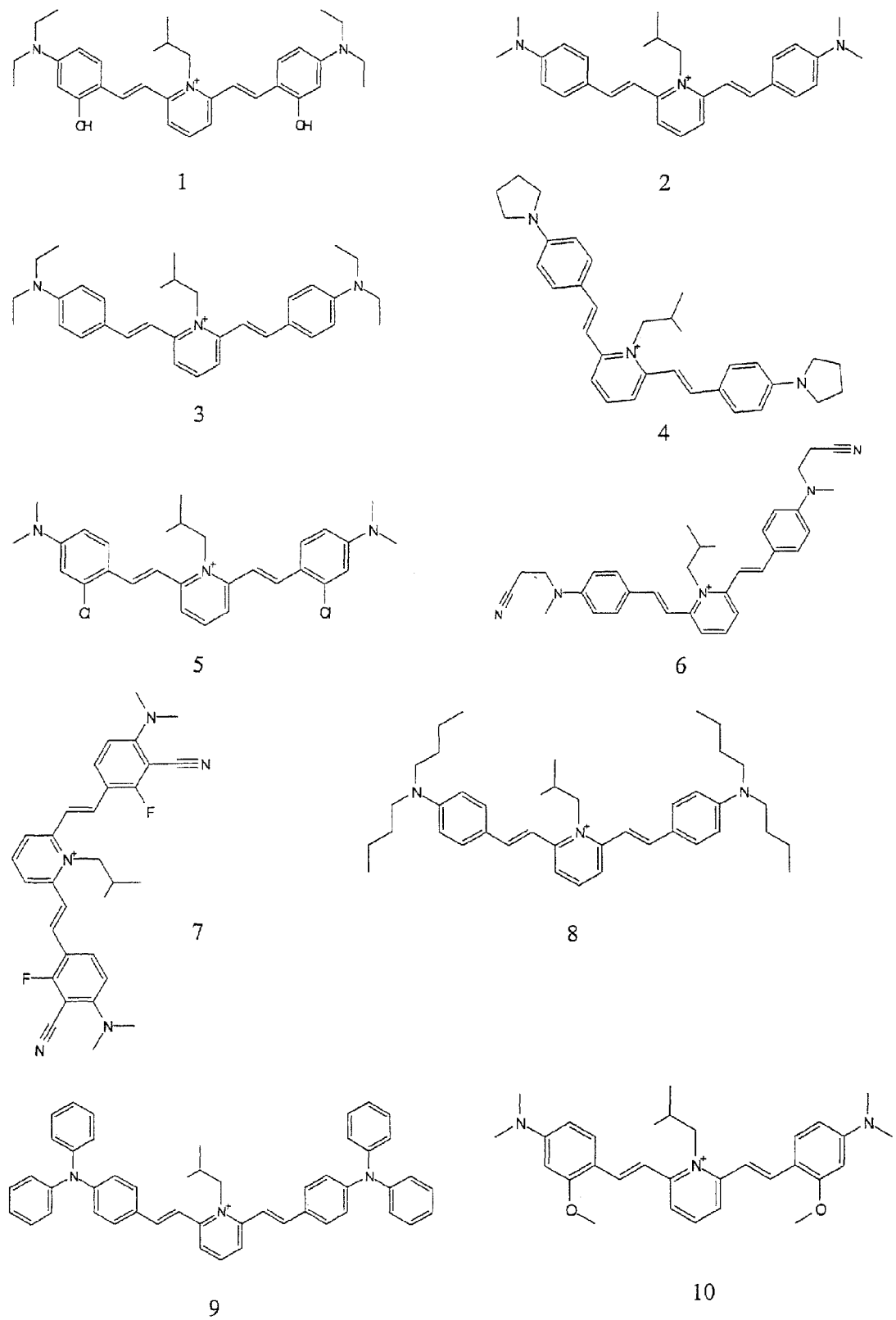
FIGS. 3A-3F illustrate compounds including an isobutyl on the pyridine ring at the nitrogen position.
Figure 3B:
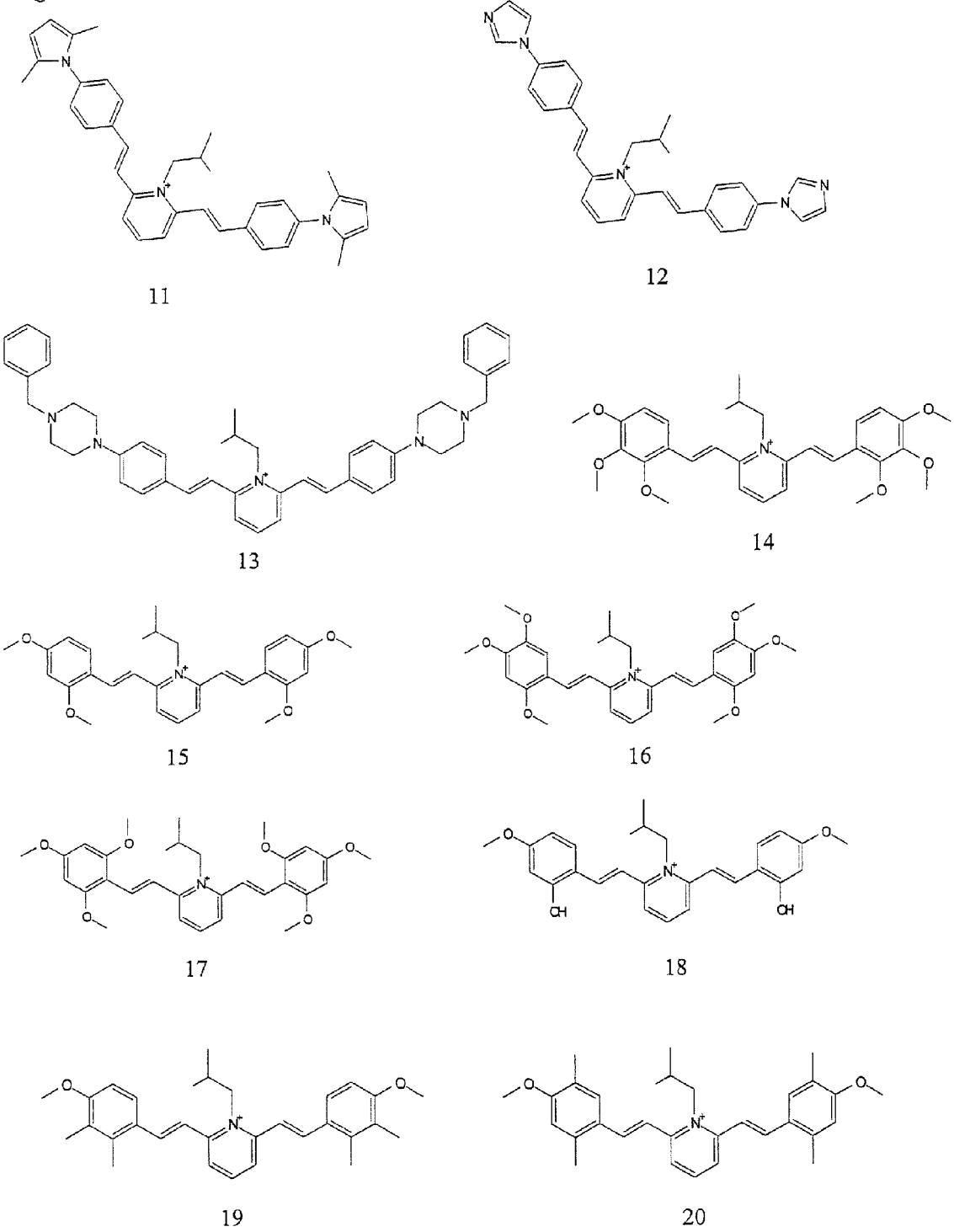
Figure 3C:
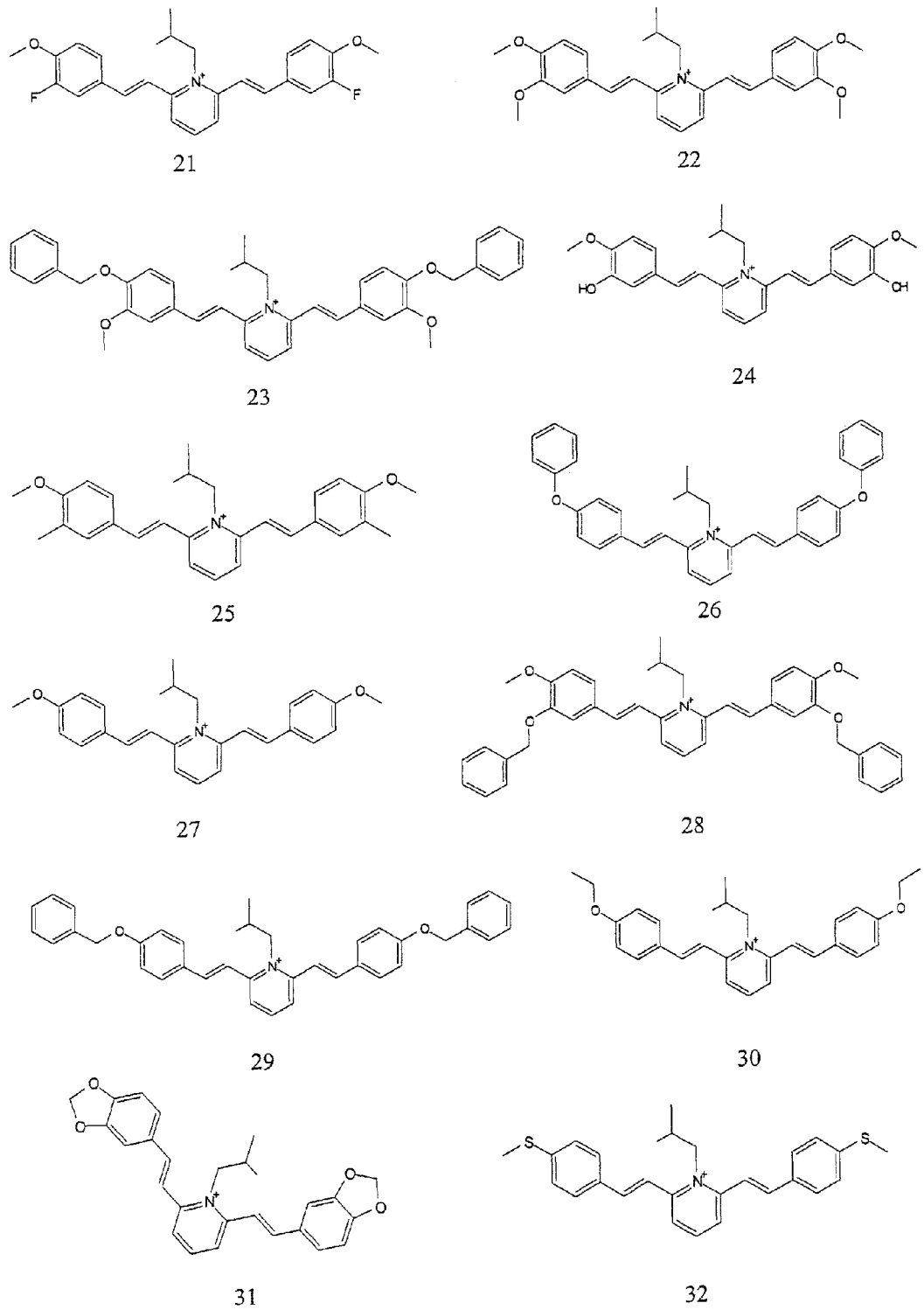
Figure 3D:
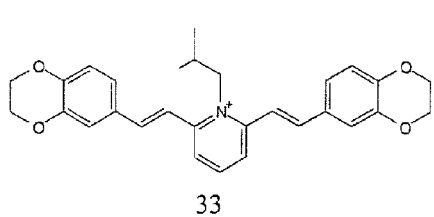
Figure 3D:
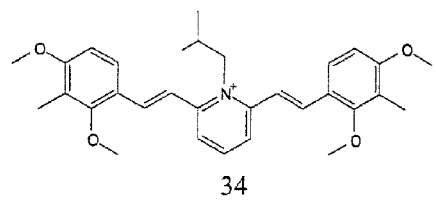
Figure 3D:
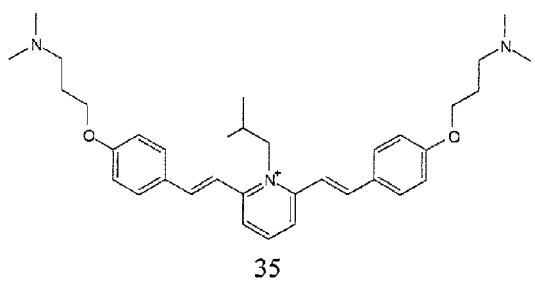
Figure 3D:
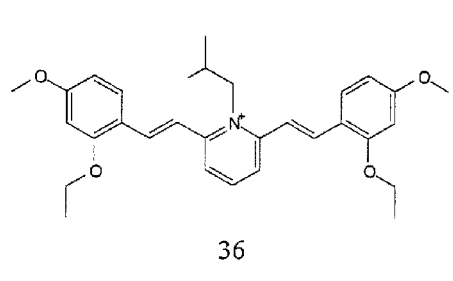
Figure 3D:
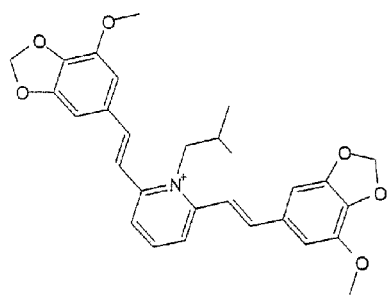
Figure 3D:
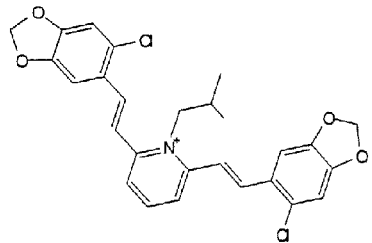
Figure 3D:
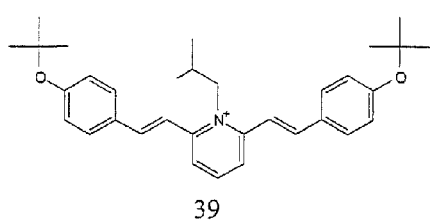
Figure 3D:
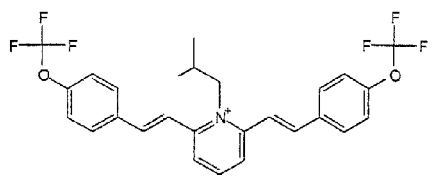
Figure 3D:
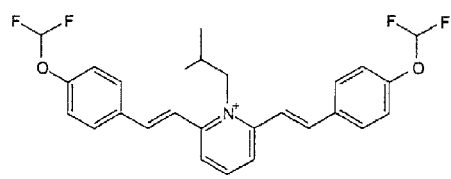
Figure 3D:
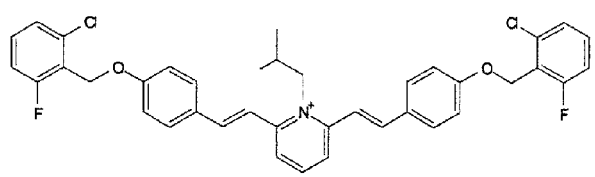
Figure 3E:
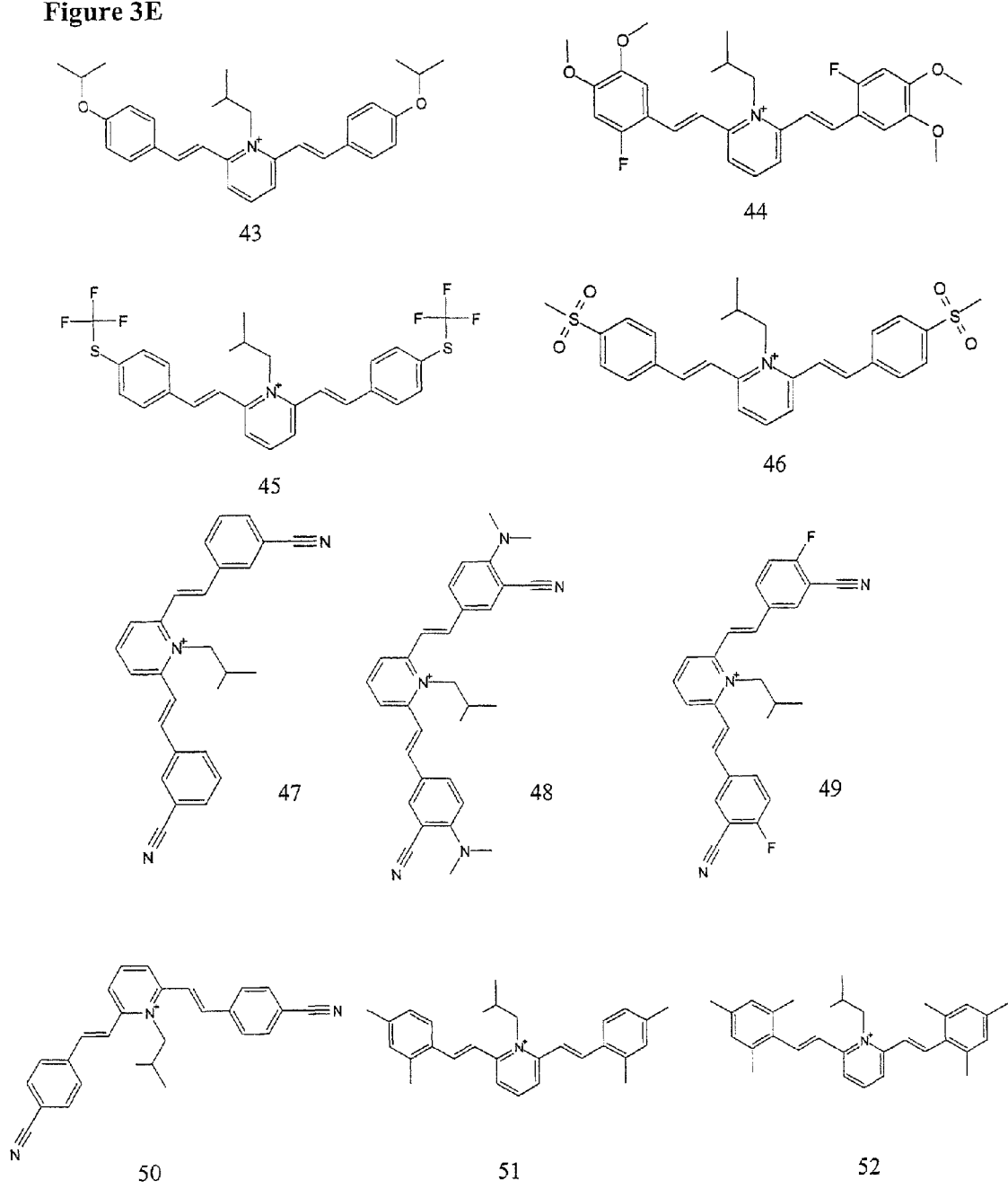
Figure 3F:
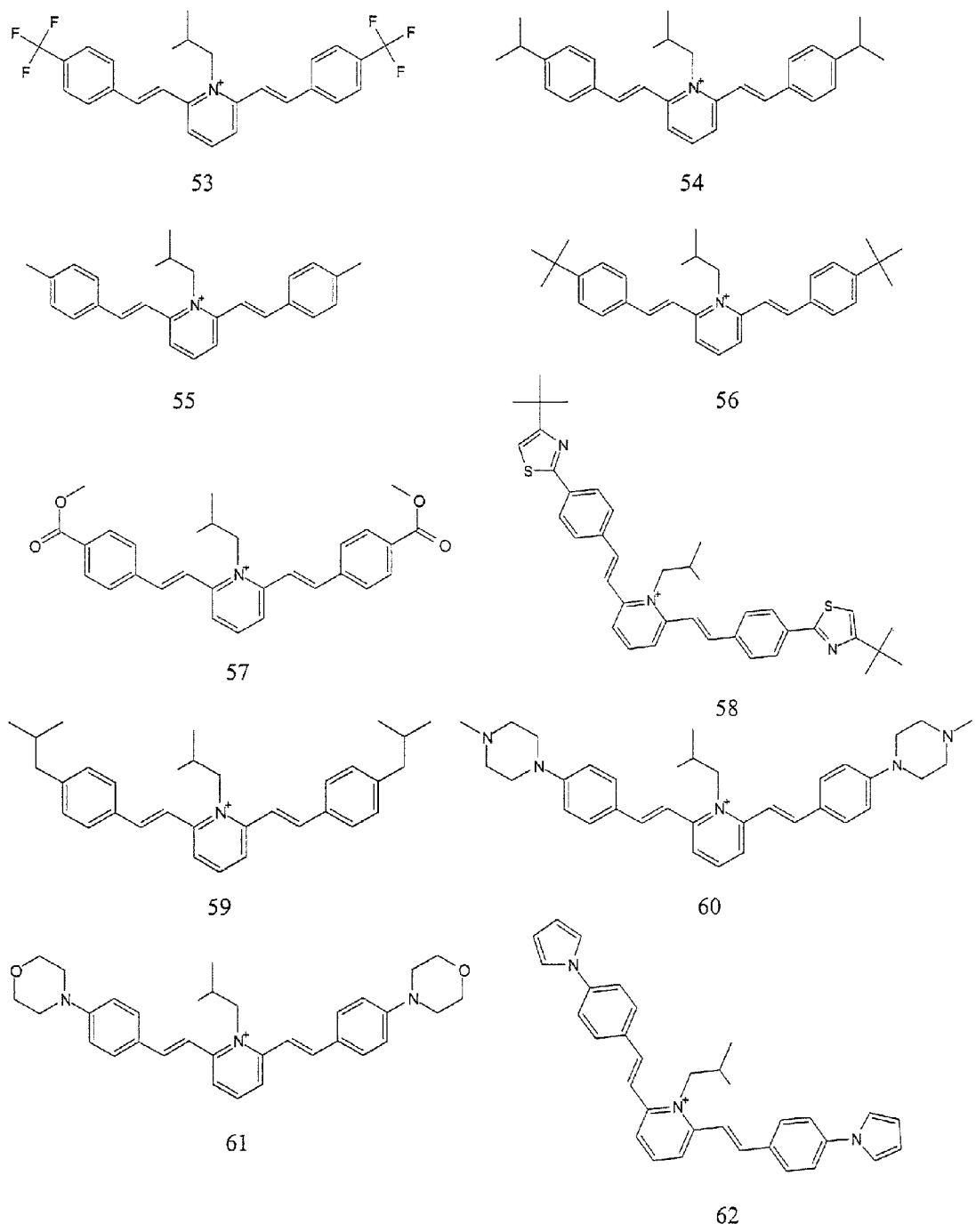
Figure 4A:
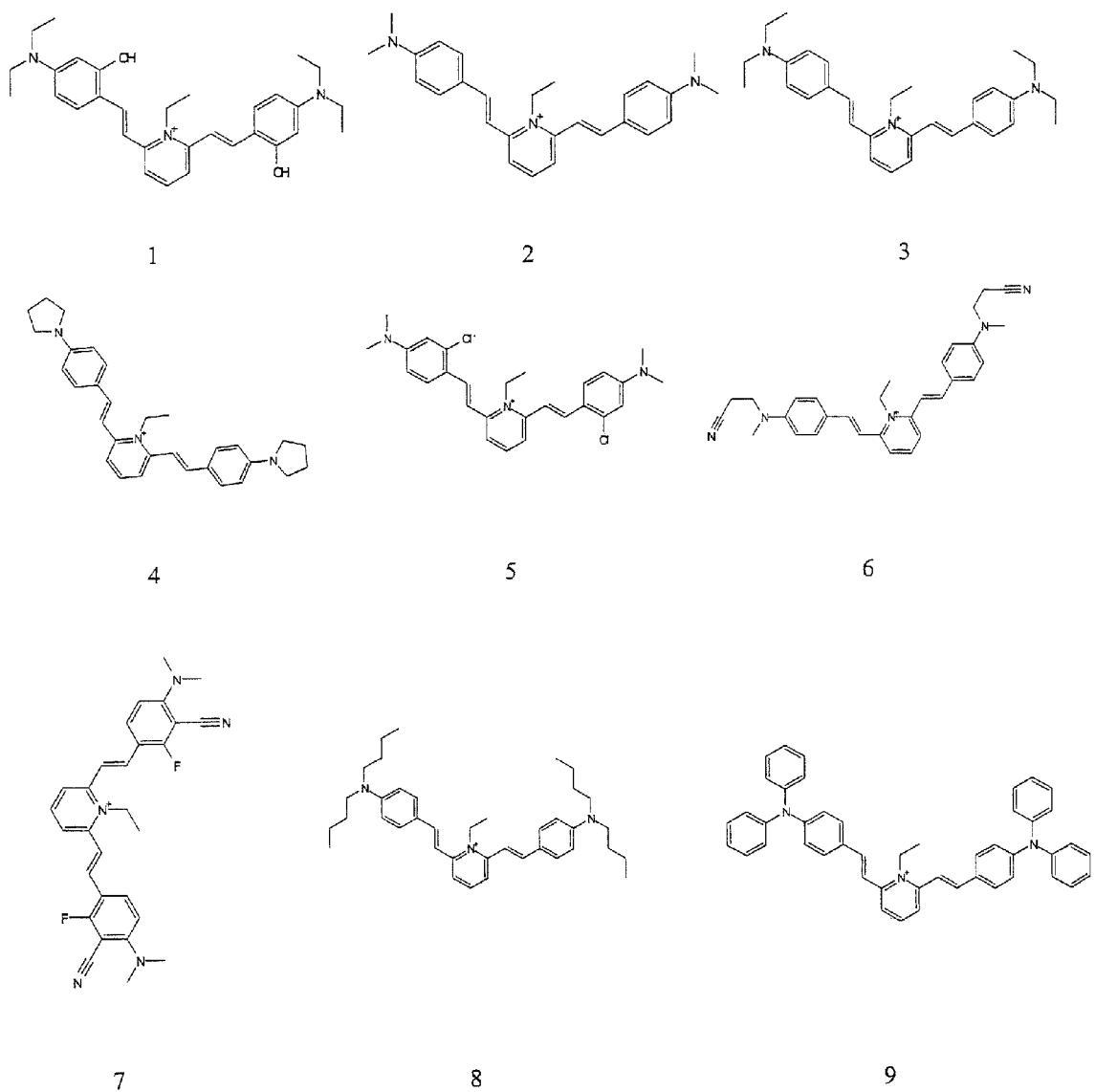
FIGS. 4A-4G depict various compounds with an ethyl attached to the pyridine ring at the nitrogen position.
Figure 4B:
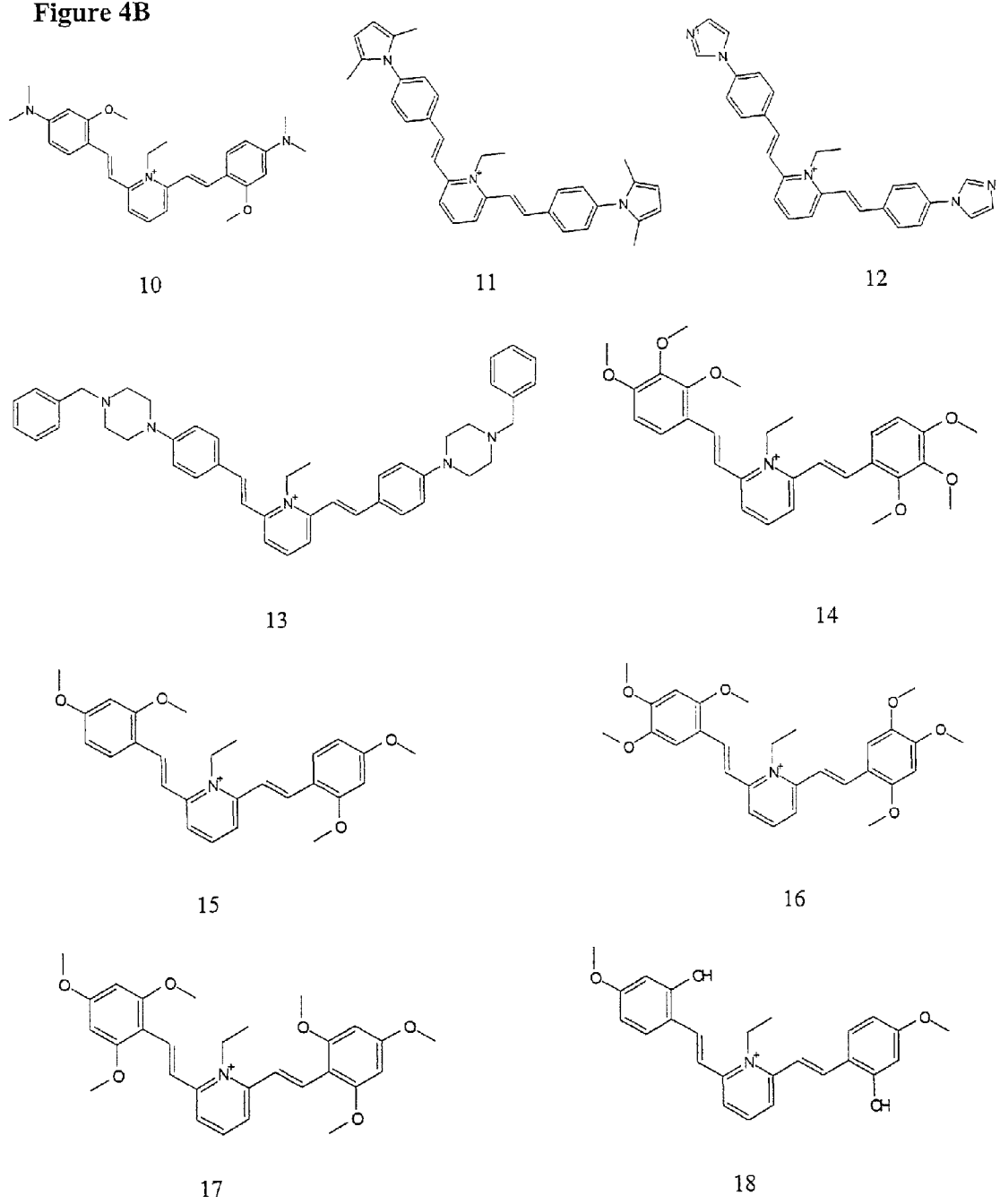
Figure 4C:
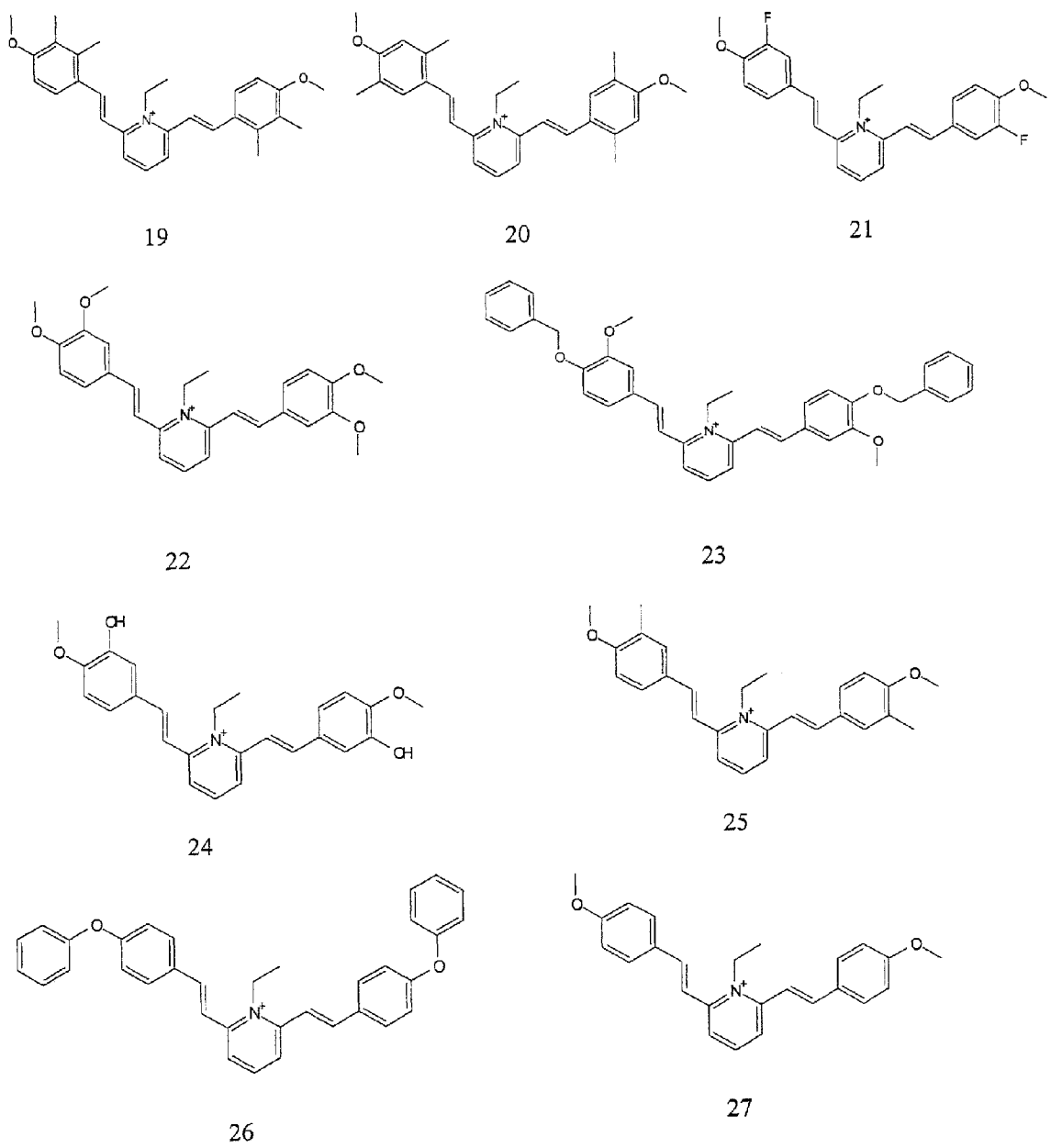
Figure 4D:
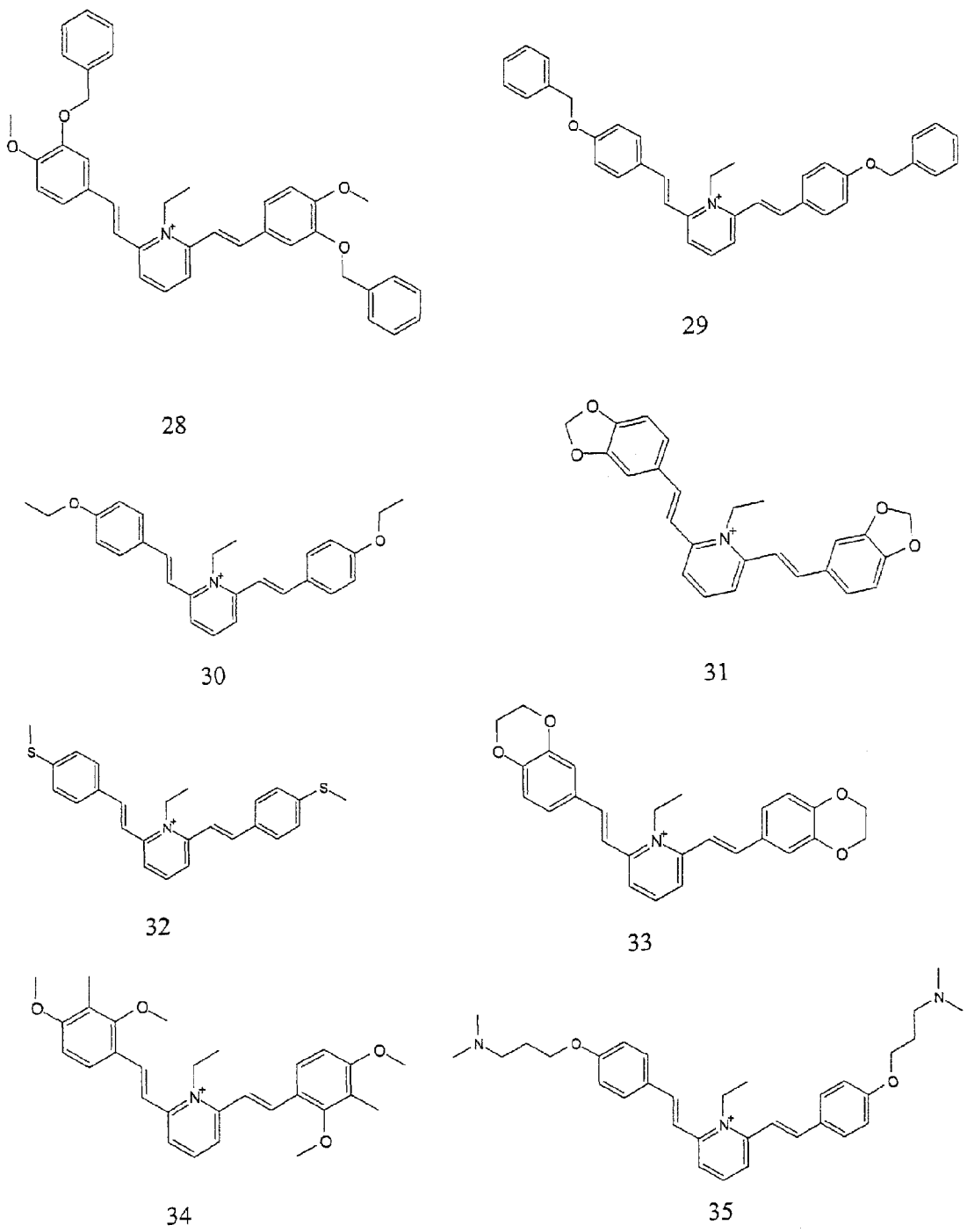
Figure 4E:
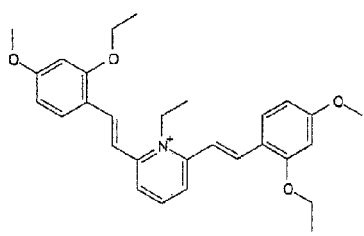
Figure 4E:
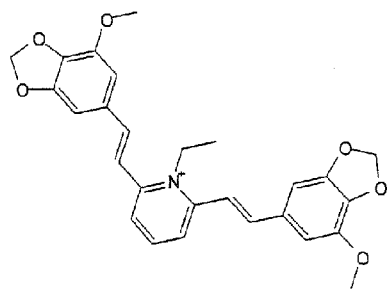
Figure 4E:
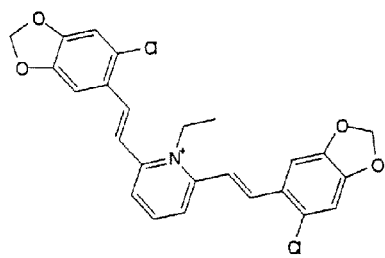
Figure 4E:
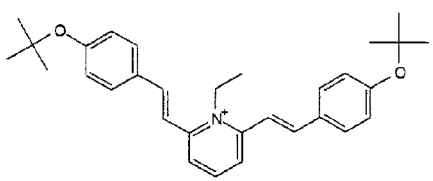
Figure 4E:
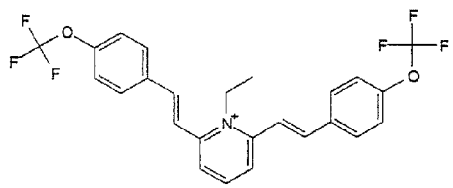
Figure 4E:
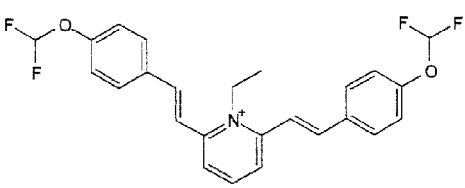
Figure 4E:
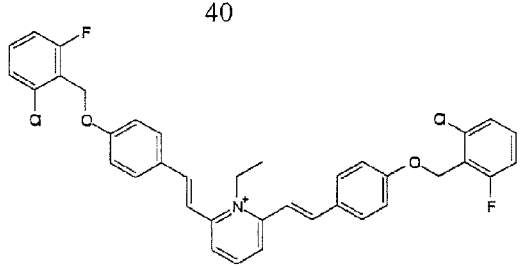
Figure 4E:
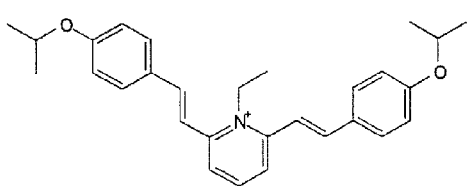
Figure 4E:
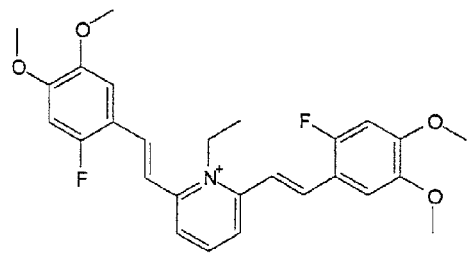
Figure 4E:
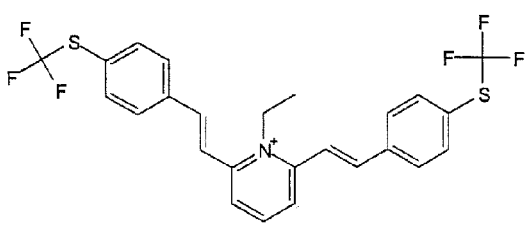
Figure 4F:
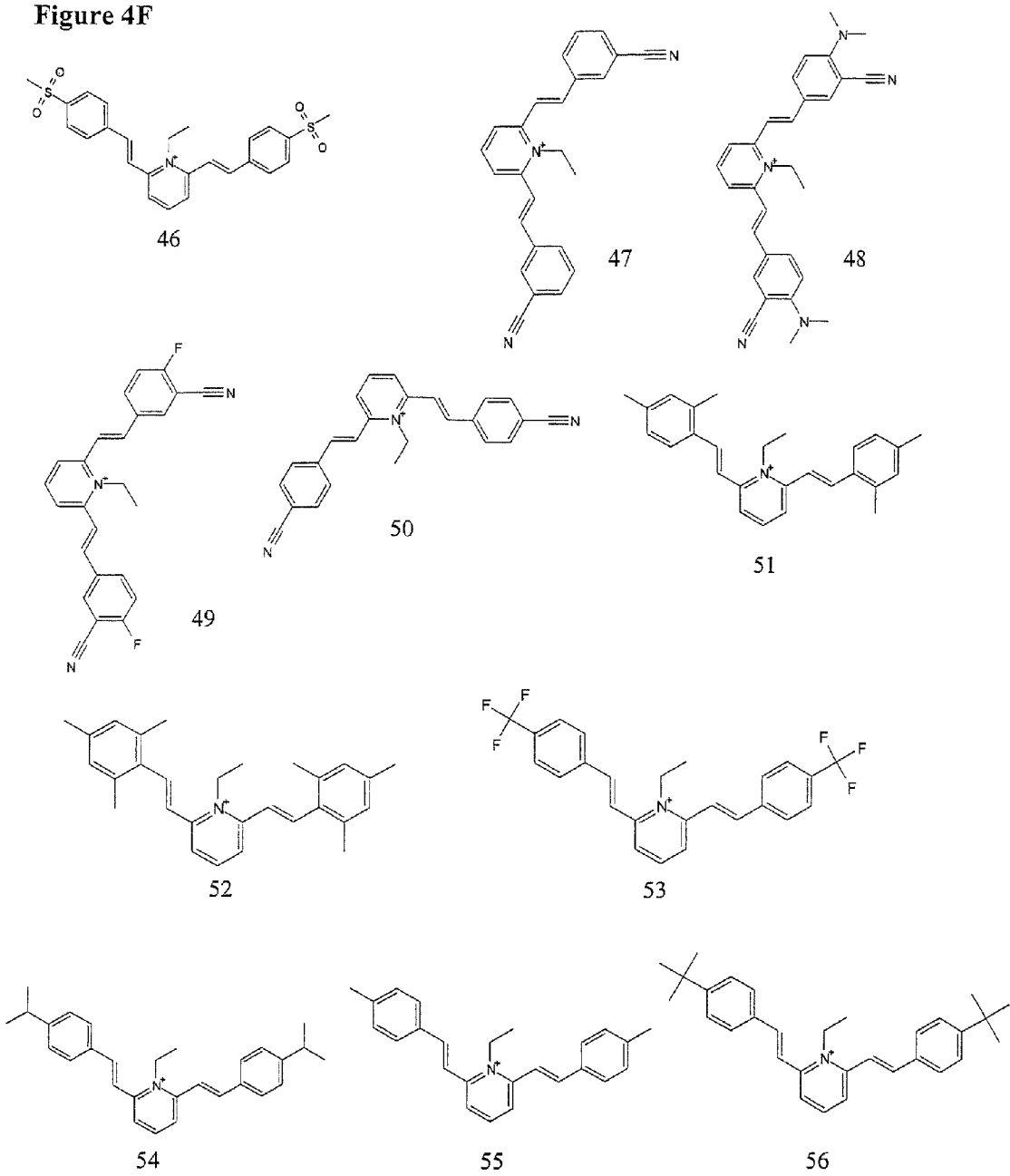
Figure 4G:
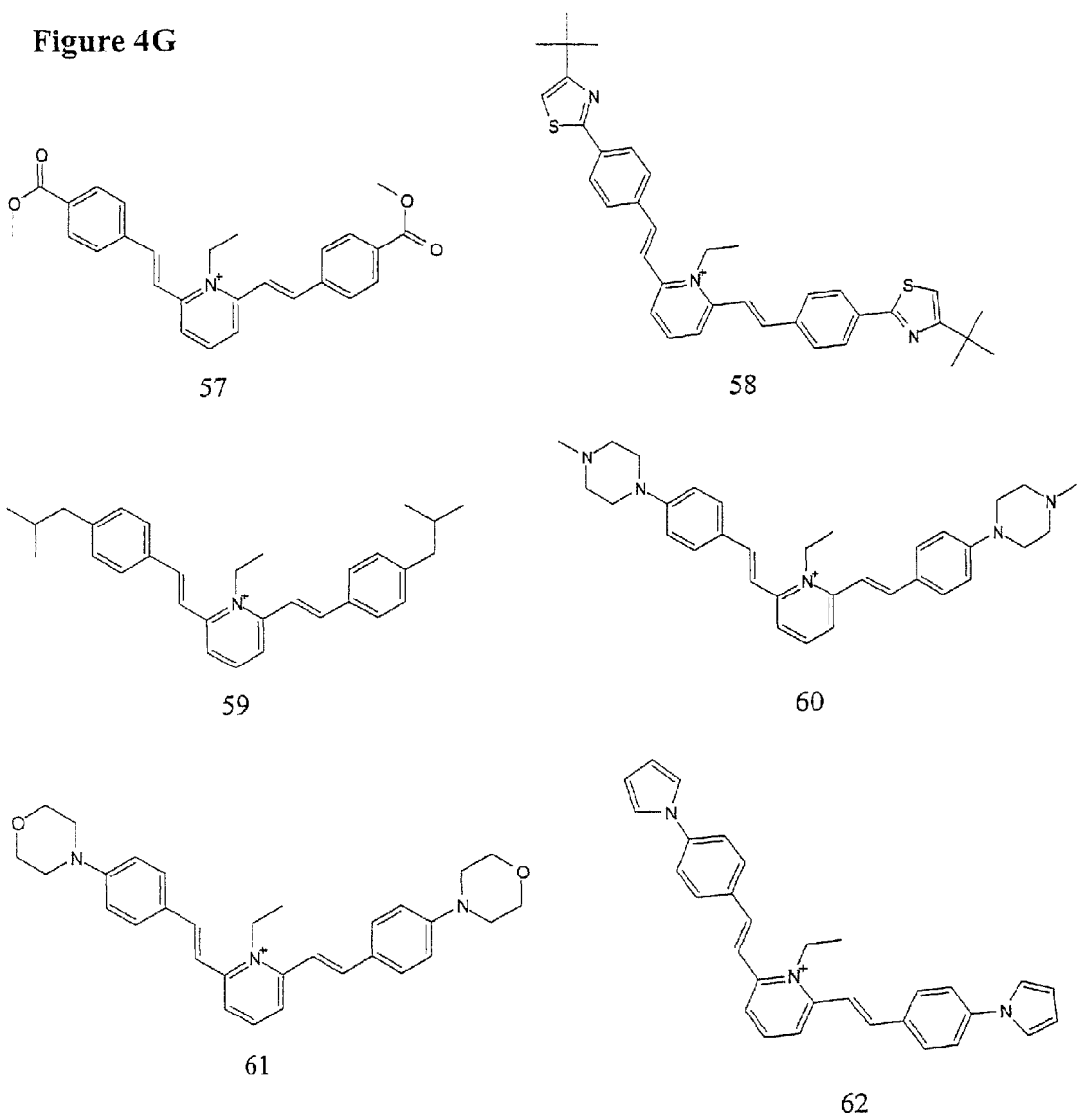

Additionally, the present invention may include compounds of the following general formula V:

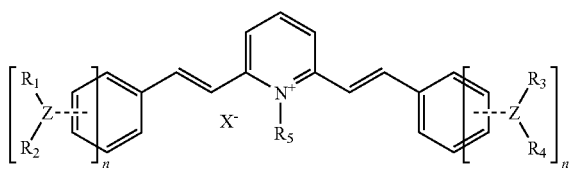

or a solvate thereof, wherein n is a number from 1 to 5, wherein Z can be present at multiple positions on the phenyl ring and is selected from the group consisting of C, N, O, S and halogen, wherein $X^-$ is an anionic salt, wherein $R_1$, $R_2$, $R_3$, or $R_4$ are independently selected from the group consisting of nothing, hydrogen, methyl, ethyl, $C_{1-10}$ alkyl (linear or branched), alkenes (linear or branched), nitriles, benzenes, pyridines, benzothiophenes, trifluoroalkyls, difluoroalkyls, substituted and unsubstituted aryl moieties and substituted and unsubstituted benzyl moieties, or wherein when $R_1$ and $R_2$ or when $R_3$ and $R_4$ are taken together with the nitrogen atom to which they are attached, they form pyrrolidino or piperidino rings. $X^-$ can be selected from the group including fluoride, chloride, bromide, iodide halide, mesylate, tosylate, napthylate, nosylate, para-aminobenzoate, benzenesulfonate, besylate, lauryl sulfate, 2,4-dihydroxy benzophenone, 2-(2-hydroxy-5'-methylphenyl)benzotriazole, ethyl 2-cyano-3,3-diphenyl acrylate and 5-butyl phenyl salicylate. $R_5$ is selected from the group consisting of methyl, ethyl, $C_{1-10}$ alkyl (linear or branched), alkenes (linear or branched), alkynes, n-propyl, i-propyl, n-butyl, i-butyl, substituted and unsubstituted aryl moieties and substituted and unsubstituted benzyl moieties. $R_5$ may also be an organometallic compound such as organotin, organosilicon, or organogermanium. Additionally, $R_5$ may be $(CH_2)_n$-$MR_6$, wherein n is a number from 1 to 6, M is an organometallic compound such as tin, silicon, or germanium, and wherein $R_6$ is a selected from the group consisting of propyl, butyl, or any alkyl compound. FIGS. 1-4 illustrate various combinations of the compounds that may be formed according to the present invention. These compounds can be in the E, E configuration and can be used for any of the methods and uses disclosed in the present application.

The compounds of the present invention are capable of existing as geometric isomers. All such isomers, individually and as mixtures, are included within the scope of the present invention for their industrial uses. The E,E isomer is one configuration of the invention, and both the cisoid and transoid 2,6-conformations of the E,E-configuration are possible. Additionally, the otho, ortho conformation of the structure can be formed in addition to the para and meta structures illustrated above. The ortho conformation structure can include the same salts and moieties as disclosed above and throughout the application.

Some of the embodiments of the present invention include 1-ethyl-(E,-E)-2,6-bis[2-[4-(pyrrolidinyl)phenyl]ethenyl]pyridinium chloride, 1-ethyl-(E,-E)-2,6-bis[p-(1-pyrrolidinostyryl]pyridinium chloride, 1-methyl-(E,-E)-2,6-bis[2-[4-(pyrrolidinyl)phenyl]ethenyl]pyridinium chloride and 1-methyl-(E,-E)-2,6-bis[p-(1-pyrrolidinostyryl]pyridinium chloride.

Compounds according to the invention can be made according to any suitable method of organic chemistry. More specifically, compounds of formula I can be prepared as outlined in U.S. Pat. No. 3,085,935, the disclosure of which is incorporated in its entirety.

Additionally, embodiments of the present invention may include the compounds produced by a synthesis that includes preparing the compounds by condensation of two equivalents of an aldehyde of formula IV.

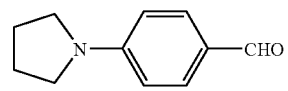

with a quaternary ammonium salt of 2,6-lutidine

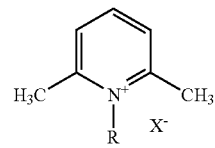

The condensation may be performed in a lower alcohol with a catalyst such as a secondary amine (e.g. piperidine). When $X^-$ in the above formula is an iodide ion (corresponding to an alkiodide salt of lutidine), the condensation product (formula I) is relatively insoluble and precipitates in the course of the reaction. The reaction yield of formula I can be nearly quantitative. Three times the amount of catalyst as stated in U.S. Pat. No. 3,085,935 can be used. Other methods may be used to produce the compound and both more or less catalyst may be employed to produce formula I.

Furthermore, it may be desirable to convert the iodide salt to the chloride salt. This conversion may be accomplished by size exclusion (molecular sieve) chromatography eluted and equilibrated with a suitable solvent containing an excess of ammonium chloride. The column effluent, containing the chloride salt can be obtained by evaporation of the solvent, along with the ammonium iodide by-product. The resulting product should be substantially free of the iodide salt. Alternatively, alkchloride salt of 2,6-lutidine can be reacted with an aldehyde of formula IV in the presence of a secondary amine (e.g. piperidine) to give the chloride salt of Formula I directly.

The present invention has surprising found that the chloride salt has an increased stability as compared to the iodide salt. Other methods known in the art may be utilized to convert the salts to UV blocker salts or surfactant salts. Other salts may include:

Formula A-Stilbazium p-aminobenzoate salt

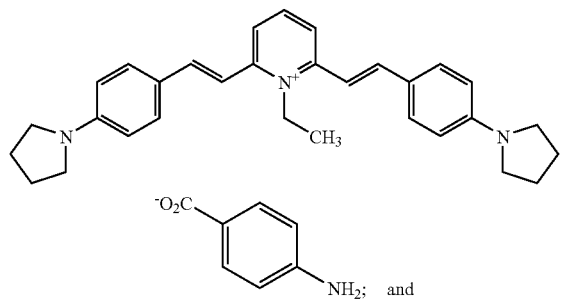

and

Formula B-Stilbazium dodecyl sulfate salt (Stilbazium lauryl sulfate salt)

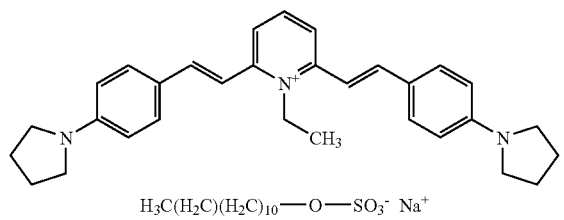

Additionally "salts" may include substituted benzophenones such as 2,4-dihydroxy benzophenone, substituted benzotriazoles, such as 2-(2-hydroxy-5'-methylphenyl)benzotriazole, substituted acrylates, such as ethyl 2-cyano-3,3-diphenyl acrylate, and salicylates, such as the 5-butyl phenyl salicylate.

The salts may include an ultraviolet blocker or a surfactant. As used herein "ultraviolet blocker" refers to all "photosensitive materials" which refers to all compositions and materials designed to block and/or absorb ultraviolet light. This term also refers to all photoprotective and photoresistant agents.

The compounds of the present invention may be used to treat all areas where molds, fungi and bacteria are grown. Examples include, but are not limited to wood, air ducts, lumber, decks, pipes, stucco, tiles, paint, insulation, roofs, building materials, metal, computer parts, food packaging, substrates, etc.

Another embodiment of the present invention can include the stilbazium compounds being encapsulated. As used herein the term "microcapsules" is intended to contemplate single molecules, encapsulated discrete particulate, multiparticulate, liquid multicore and homogeneously dissolved active components. The encapsulation method may provide either a water soluble or oil soluble active component encapsulated in a shell matrix of either a water or oil soluble material. The microencapsulated active component may be protected from oxidation and hydration, and may be released by melting, rupturing, biodegrading, or dissolving the surrounded shell matrix or by slow diffusion of the active component through the matrix. Microcapsules usually fall in the size range of between 1 and 2000 microns, although smaller and larger sizes are known in the art.

The compound of the present invention may be placed in a microcapsule or hollow fiber type used for distribution. They may also be dispersed in a polymeric material or held as a liquid.

An active ingredient may be placed with the compound of the present invention in a microcapsule. Examples of the active ingredient having repellent activity may include triethylene glycol monohexyl ether and N,N-diethyl-m-triamide. Examples of the active ingredient having aromatic activity include geraniol, limonene, benzyl alcohol, esters of a $C_{6-20}$ hydrocarbon, ethers, aldehydes and alcoholic compounds. Examples of the active ingredient having pesticidal activity include insecticides such as salithion, diazinon and chlorpyrifos and bactericides such as thiophanate-methyl and captan.

Such constituents can be encapsulated, as is desired in the case of phase change materials. Such encapsulated constituents can further be encapsulated in microcapsules. The microcapsules can be made from a wide variety of materials, including polyethylene, polypropylenes, polyesters, polyvinyl chloride, tristarch acetates, polyethylene oxides, polypropylene oxides, polyvinylidene chloride or fluoride, polyvinyl alcohols, polyvinyl acetates, urethanes, polycarbonates, and polylactones. Further details on microencapsulation are to be found in U.S. Pat. Nos. 5,589,194 and 5,433,953, the contents of which are incorporated herein in their entirety. Microcapsules suitable for use in the base materials of the present invention have diameters from about 1.0 to 2,000 microns.

No particular limitation is imposed on the shape for holding the active ingredient. In other words, there are various forms for holding the active ingredient by a holding mixture. Specific examples include microcapsules in which the surface of the active ingredient has been covered with the holding mixture; and products processed into a desired shape, each being obtained by kneading the active ingredient in the holding mixture or forming a uniform solution of the holding mixture and the active ingredient, dispersing the active ingredient in the holding mixture by the removal of the solvent or the like and then processing the dispersion into a desired shape such as single molecule, liquid, sphere, sheet, film, rod, pipe, thread, tape or chip. In addition, these processed products having a surface covered with a barrier layer for controlling the release of the active ingredient and those coated with an adhesive for improving applicability can be given as examples. As further examples, those obtained by filling the active ingredient in the holding mixture processed into a form of a capillary tube, heat sealing both ends of the capillary tube and then encapsulating the active ingredient therein; and those obtained by centrally cutting the above-mentioned capillary tube into two pieces, thereby having each one end as an opening.

The container formed of a holding mixture which container has an active ingredient enclosed therein as a liquid phase to secure uniform release ability over a long period of time. As such shape, tube-, bottle- or bag-shaped container is used generally.

When the mixture is formed into a container, the sustained release layer desirably has a thickness of at least 0.002 mm for effecting stable sustained release. There occurs no particular problem when the sustained release layer has a thickness not smaller than 0.002 mm, but that ranging from 0.005 mm to 5 mm can be used. When it exceeds 5 mm, the release amount of the compound tends to become too small.

For solids, the release surface area of the sustained release preparation formed of such a container is desirably 0.001 cm$^2$ or larger. A range of from 0.01 cm$^2$ to 1 cm$^2$ may be used.

When the active ingredient is enclosed and held in a container of the sustained release preparation, said container having been formed of a holding mixture, it may be enclosed in portions. The enclosed amount can be 0.5 mg to 5 mg, and may be 1 mg, 2 mg, 3 mg, or 4 mg.

As the shape of the container formed of a holding mixture, a tube, bottle and bag can be used. In the case of the tube-shaped preparation, that having an internal diameter of 0.4 mm to 10 mm can be used. Internal diameters smaller than 0.4 mm make it difficult to fill the active ingredient in the container, while those larger than 10 mm make it difficult to conduct encapsulation. The bottle-shaped preparation is formed by blow molding or injection molding and generally has an internal volume of 0.1 to 200 ml. The bottle having an internal volume less than 0.1 ml cannot be formed easily, while that having an internal volume greater than 200 ml is not economical because there is a large difference between the amount of the active ingredient filled therein and the internal volume. In the case of a bag-shaped preparation, the amount of the active ingredient filled in the bag is desirably 1 mg to 100 g.

The biodegradable sustained-release preparation according to the first group of the present invention should retain its essential performance during application so that a pigment or dye, or various stabilizers such as ultraviolet absorber/blocker or antioxidant may be added to the holding mixture in order to improve the weather resistance. Alternatively, it is possible to add such an additive to the active ingredient enclosed in the container formed of a holding mixture.

As used herein, the term "controlled release" is intended to mean the release of a bio-active at a pre-selected or desired rate. This rate will vary depending upon the application. Desirable rates include fast or immediate release profiles as well as delayed, sustained or sequential release profiles. Combinations of release patterns, such as initial spiked release followed by lower levels of sustained release of the bio-active are also contemplated by the present invention.

As used herein, the term "bio-active" includes therapeutic agents such as pharmaceutical or pharmacological active agents, e.g., drugs and medicaments, as well as prophylactic agents, diagnostic agents and other chemicals or materials useful in treating or preventing conditions, infections and/or diseases. The compositions of the present invention are particularly effective in plants and other organisms.

In accordance with the present invention there is provided a microcapsule bacteriocide and/or fungicide composition comprising microcapsules each having a polyurea shell including as an integral part of said shell a photostable ultraviolet light absorbent compound or blocker compound having a log molar extinction coefficient of from about 2 to 5 with respect to radiation having wave lengths in the range of from about 270 to 350 nanometers and a liquid fill capable of slowly permeating the shell and comprising a pyridinium salt and a biological synergist therefor.

As used herein "photosensitive material" refers to all compositions and materials designed to block and/or absorb ultraviolet light. This term also refers to all photoprotective and photoresistant agents.

As herein used "surfactant" refers to all compositions including surfactant salt compositions that are capable of forming emulsions, micro-emulsions, suspensions, etc.

The entire microcapsule composition can include of 60-90 percent of liquid fill and 40-10 percent of shell wall, the liquid fill comprising 5-40 percent of pyridinium salt, 25-50 percent of biological synergist and 20-40 percent of a water-immiscible organic solvent and the shell including as an integral part thereof 0.5-20 percent of photostable ultraviolet light absorbent compound (all percentages being based on the weight of the entire microcapsule composition).

The pyridinium salt remains inside the microcapsules while the composition is packaged and in storage, i.e., in a closed container due to the partial pressure of the pyridinium salt surrounding the microcapsules. When the product is applied as a bacteriocide and/or fungicide, the pyridinium salt, releases slowly (the actual speed of release depending upon the thickness and porosity of the capsule walls). The pyridinium salt is chemically stable during storage and after application until it permeates the capsule walls. At that time it becomes available as a bacteriocide and/or fungicide until degraded. Since the fill permeates the shell wall slowly, the microcapsule product has a long effective bacteriocide and/or fungicide life and may be stored for extended periods (e.g. for 6 months and more).

Suitable fill stabilizers absorb ultraviolet radiation in the range of about 270-350 nanometers and convert it to a harmless form. They have a high absorption coefficient in the near ultraviolet portion of the spectrum (e.g. a log molar extinction coefficient of from about 2 to 5) but only minimal absorption in the visible portion of the spectrum. They do not exhibit any substantial chemical reaction with the isocyanate groups and primary amine groups of the shell forming compounds during the microencapsulation process. Among the compounds which can be used as fill stabilizers are substituted benzophenones such as 2,4-dihydroxy benzophenone, 2-hydroxy-4-methoxy benzophenone, 2-hydroxy-4-octyloxy benzophenone, etc.; the benzotriazoles such as 2-(2-hydroxy-5'-methylphenyl)benzotriazole, 2-(3',5'-diallyl-2'-hydroxylphenyl)benzotriazole, etc.; substituted acrylates such as ethyl 2-cyano-3,3-diphenyl acrylate, 2-ethylhexyl-2-cyano-3,3-diphenyl acetate, etc.; salicylates such as phenyl salicylates, 5-butyl phenyl salicylate, etc.; and nickel organic compounds such as nickel bis(octylphenol)sulfide, etc. Additional examples of each of these classes of fill stabilizers may be found in Kirk-Othmer, Encyclopedia of Chemical Technology. The fill stabilizers may comprise up to 5 percent, and are generally from about 0.01 to 2 percent, by weight of the microcapsule composition.

The embodiments of the invention also provide a process for controlling fungal and bacterial activity by contacting the fungi and bacteria with an effective level of the compositions comprising stilbazium compound as recited throughout. Contact may be accomplished directly, for example, by atomization of the composition into the air in the form of a spray. Alternatively, compositions of the present invention may be provided in various other forms, for example in sheet materials carrying the microcapsules, (e.g. tapes coated or impregnated with the microcapsules) that may be placed in areas where the fungi and bacteria may grow.

Another embodiment of the present invention may include heat sensitive materials which are excellent in preservation stability especially in resistance to light, and microcapsules having an ultraviolet absorber enclosed therein, which are applicable to various fields. Desirable constituents which may be present in a base material include materials which can absorb heat and protect an underlying material from overheating. Thermal energy is absorbed by the phase change of such materials without causing an increase in the temperature of these materials. Suitable phase change materials include paraffinic hydrocarbons, that is, straight chain hydrocarbons represented by the formula $C_nH_{n+2}$, where n can range from 13 to 28. Other compounds which are suitable for phase change materials are 2,2-dimethyl-1,3-propane diol (DMP), 2-hydroxymethyl-2-methyl-1,3-propane diol (HMP) and similar compounds. Also useful are the fatty esters such as methyl palmitate. Phase change materials that can be used include paraffinic hydrocarbons.

Heat sensitive recording materials are well known which utilize a color forming reaction between a colorless or light-colored basic dye and an organic or inorganic color acceptor to obtain record images by thermally bringing the two chromogenic substances into contact with each other. Such heat sensitive recording materials are relatively inexpensive, are adapted for use with recording devices which are compact and easy to maintain, and have therefore found wide applications as recording media for facsimile systems, various computers, etc. In order to improve light resistance of heat sensitive recording materials a finely divided ultraviolet absorber or blocker can be added to the heat sensitive recording layer or protective layer.

Another embodiment of the present invention is to provide microcapsules which have excellent retainability of ultraviolet absorber, difficult to be ruptured at a usual pressure and are excellent in ultraviolet ray absorbing efficiency.

Embodiments of the present invention can include a heat sensitive recording material comprising a substrate, a recording layer formed over the substrate and containing a colorless or light-colored basic dye and a color acceptor, and a protective layer formed over the recording layer, the recording material being characterized in that microcapsules having an ultraviolet absorber enclosed therein and having substantially no color forming ability are incorporated in the protective layer.

Further, the present invention provides microcapsules having an ultraviolet absorber and as required an organic solvent enclosed therein, which have capsule wall film of synthetic resin and mean particle size of 0.1 to 3 μm.

The following are examples of ultraviolet absorbers that may be used in the present invention.

Phenyl salicylate, p-tert-butylphenyl salicylate, p-octylphenyl salicylate and like salicylic acid type ultraviolet absorbers; 2,4-dihydroxybenzophenone, 2-hydroxy-4-methoxybenzophenone, 2-hydroxy-4-octyloxybenzophenone, 2-hydroxy-4-dodecyloxybenzophenone, 2,2'-dihydroxy-4-methoxybenzophenone, 2,2,'-dihydroxy-4,4'-dimethoxybenzophenone, 2-hydroxy-4-methoxy-5-sulfobenzophenone and like benzophenone type ultraviolet absorbers; 2-ethylhexyl 2-cyano-3,3-diphenyt-acrylate, ethyl 2-cyano-3,3-diphenylacrylate and like cyanoacrylate type ultraviolet absorbers; bis(2,2,6,6-tetramethyl-4-piperidyl)sebacate, bis (2,2,6,6-tetramethyl-4-piperidyl)succinate, bis(1,2,2,6,6-pentamethyl-4-piperidyl) 2-(3,5-di-tert-butyl-4-hydroxy-benzyl)-2-n-butyl malonate and like hindered amine type ultraviolet absorbers; 2-(2'-hydroxyphenyl)benzotriazole, 2-(2'-hydroxy-5'-methylphenyl)benzotriazole, 2-(2'-hydroxy-5-tert-butylphenyl)benzotriazole, 2-(2'-hydroxy-3',5'-di-tert-butylphenyl)benzotriazole, 2-(2'-hydroxy-3'-tert-butyl-5'-methylphenyl)-5-chlorobenzotriazole, 2-(2'-hydroxy-3',5'-di-tert-butylphenyl)-5-chlorobenzotriazole, 2-(2'-hydroxy-3',5'-di-tert-butylphenyl)-5-tert-butylbenzotriazole, 2-(2'-hydroxy-3',5'-di-tert-amylphenyl)benzotriazole, 2-(2'-hydroxy-3',5'-di-tert-amylphenyl)-5-tert-amylbenzotriazole, 2-(2'-hydroxy-3',5'-di-tert-amylphenyl)-5-methoxybenzotriazole, 2-[2'-hydroxy-3'-(3",4",5",6"-tetrahydrophthalimido-methyl)-5'-methylphenyl]benzotriazole, 2-(2'-hydroxy-5'-tert-octylphenyl)benzotriazole, 2-(2'-hydroxy-3'-sec-butyl-5'-tert-butylphenyl)benzotriazole, 2-(2'-hydroxy-3'-tert-amyl-5'-phenoxyphenyl)-5-methylbenzotriazole, 2-(2'-hydroxy-5'-n-dodecylphenyl)benzotriazole, 2-(2'-hydroxy-5'-sec-octyloxyphenyl)-5-phenylbenzotriazole, 2-(2'-hydroxy-3'-tert-amyl-5'-phenylphenyl)-5-methoxybenzotriazole, 2-[2'-hydroxy-3',5'-bis(α,α-dimethylbenzyl)phenyl]benzotriazole and like benzotriazole type ultraviolet absorbers which are solid at ordinary temperature; 2-(2'-Hydroxy-3'-dodecyl-5'-methylphenyl)-benzotriazole, 2-(2'-hydroxy-3'-undecyl-5'-methylphenyl)-benzotriazole, 2-(2'-hydroxy-3'-tridecyl-5'-methylphenyl)-benzotriazole, 2-(2'-hydroxy-3'-tetradecyl-5'-methylphenyl)-benzotriazole, 2-(2'-hydroxy-3'-pentadecyl-5'-methylphenyl)-benzotriazole, 2-(2'-hydroxy-3'-hexadecyl-5'-methylphenyl)-benzotriazole, 2-[2'-hydroxy-4'-(2"-ethylhexyl)oxyphenyl]-benzotriazole, 2-[2'-hydroxy-4'-(2"-ethylheptyl)oxyphenyl]-benzotriazole, 2-[2'-hydroxy-4'-(2"-ethyloctyl)oxyphenyl]-benzotriazole, 2-[2'-hydroxy-4'-(2"-propyloctyl)oxyphenyl]-benzotriazole, 2-[2'-hydroxy-4'-(2"-propylheptyl)oxyphenyl]-benzotriazole, 2-[2'-hydroxy-4'-(2"-propylhexyl)oxyphenyl]-benzotriazole, 2-[2'-hydroxy-4'-(1"-ethylhexyl)oxyphenyl]-benzotriazole, 2-[2'-hydroxy-4'-(1"-ethylheptyl)oxyphenyl]-benzotriazole, 2-[2'-hydroxy-4'-(1"-ethyloctyl)oxyphenyl]-benzotriazole, 2-[2'-hydroxy-4'-(1"-propyloctyl)oxyphenyl]-benzotriazole, 2-[2'-hydroxy-4'-(1"-propylheptyl)oxyphenyl]-benzotriazole, 2-[2'-hydroxy4'-(1"-propylhexyl)oxyphenyl]-benzotriazole, 2-(2'-hydroxy-3'-sec-butyl-5'-tert-butylphenyl-5-n-butyl-benzotriazole, 2-(2'-hydroxy-3'-sec-butyl-5'-tert-butylphenyl)-5-tert-pentyl-benzotriazole, 2-(2'-hydroxy-3'-sec-butyl-5'-tert-butylphenyl)-5-n-pentyl-benzotriazole, 2-(2'-hydroxy-3'-sec-butyl-5'-tert-pentylphenyl)-5-tert-butylbenzotriazole, 2-(2'-hydroxy-3'-sec-butyl-5'-tert-pentylphenyl)-5-n-butylbenzotriazole, 2-(2'-hydroxy-3',5'-di-tert-butylphenyl)-5-sec-butylbenzotriazole, 2-(2'-hydroxy-3',5'-di-tert-pentylphenyl)-5-sec-butylbenzotriazole, 2-(2'-hydroxy-3'-tert-butyl-5'-tert-pentylphenyl)-5-sec-butylbenzotriazole, 2-(2'-hydroxy-3',5'-di-sec-butylphenyl)-5-chlorobenzotriazole, 2-(2'-hydroxy-3',5'-di-sec-butylphenyl)-5-methoxybenzotriazole, 2-(2'-hydroxy-3',5'-di-sec-butylphenyl)-5-tert-butylbenzotriazole, 2-(2'-hydroxy-3',5'-di-sec-butylphenyl)-5-n-butylbenzotriazole, octyl 5-tert-butyl-3-(5-chloro-2H-benzotriazole-2-yl)-4-hydroxybenzene-propionate, condensate of methyl 3-[3-tert-butyl-5-(2H-benzotriazole-2-yl)-4-hydroxyphenyl] propionate and polyethylene glycol (molecular weight: about 300) and like benzotriazole type ultraviolet absorbers which are liquid at ordinary temperature. Of course, the ultraviolet absorber is not limited to thereabove and can be used as required in a mixture of at least two of them.

Although the amount of ultraviolet absorber to be used is not limited specifically, the amount can be adjusted to 10 to 500 parts by weight, and generally from to 20 to 250 parts by weight of the ultraviolet absorber versus the active ingredient.

The microcapsules for use in the present invention can be prepared by various known methods. They are prepared generally by emulsifying and dispersing the core material (oily liquid) comprising an ultraviolet absorber and, if necessary, an organic solvent in an aqueous medium, and forming a wall film of high-molecular-weight substance around the resulting oily droplets.

Examples of useful high-molecular-weight substances for forming the wall film of microcapsules are polyurethane resin, polyurea resin, polyamide resin, polyester resin, polycarbonate resin, aminoaldehyde resin, melamine resin, polystyrene resin, styrene-acrylate copolymer resin, styrene-methacrylate copolymer resin, gelatin, polyvinyl alcohol, etc. Especially, microcapsules having a wall film of a synthetic resin, particularly polyurea resin, polyurethane resin and aminoaldehyde resin among other resins have excellent retainability of an ultraviolet absorber and high heat resistance and accordingly exhibit the outstanding additional effect to serve the function of a pigment which is to be incorporated in the protective layer for preventing sticking to the thermal head. Moreover, microcapsules having a wall film of polyurea resin or polyurethane resin are lower in refractive index than microcapsules with wall films of other materials and usual pigments, are spherical in shape and are therefore usable favorably because even if present in a large quantity in the protective layer, they are unlikely to reduce the density of record images (so-called whitening) owing to irregular reflection of light. Further, polyurea resin and polyurethane resin are more elastic than aminoaldehyde resin and therefore polyurea resin and polyurethane resin are generally used as a wall film for microcapsules which are used under a condition of high pressure. On the other hand, microcapsules having a wall film made from aminoaldehyde resin have a merit that the wall film can be controlled in thickness without depending on particle size of emulsion because the microcapsules can be prepared by adding a wall-forming material after emulsification of a core material.

The present invention may also include organic solvent together with an ultraviolet absorber. The organic solvent is not particularly limited and various hydrophobic solvents can be used which are used in a field of pressure sensitive manifold papers. Examples of organic solvents are tricresyl phosphate, octyldiphenyl phosphate and like phosphates, dibutyl phthalate, dioctyl phthalate and like phthalates, butyl oleate and like carboxylates, various fatty acid amides, diethylene glycol dibenzoate, monoisopropylnaphthalene, diisopropylnaphthalene and like alkylated naphthalenes, 1-methyl-1-phenyl-1-tolylmethane, 1-methyl-1-phenyl-1-xylylmethane, 1-phenyl-1-tolylmethane and like alkylated benzenes, isopropylbiphenyl and like alkylated biphenyls, trimethylolpropane triacrylate and like acrylates, ester of polyol and unsaturated carboxylic acid, chlorinated paraffin and kerosene. These solvents can be used individually or in a mixture of at least two of them. Among these hydrophobic media having a high boiling point, tricresyl phosphate and 1-phenyl-1-tolylmethane are desirable since they exhibit high solubility in connection with the ultraviolet absorber to be used in the present invention. Generally, the lower the viscosity of the core material, the smaller is the particle size resulting from emulsification and the narrower is the particle size distribution, so that a solvent having a low boiling point is conjointly usable to lower the viscosity of the core material. Examples of such solvents having a low boiling point are ethyl acetate, butyl acetate, methylene chloride, etc.

The amount of organic solvent to be used should be suitably adjusted according to the kind and amount of ultraviolet absorber to be used and the kind of organic solvent and is not limited specifically. For example in case of using an ultraviolet absorber which is liquid at ordinary temperature, an organic solvent is not necessarily used. However, in case of using an ultraviolet absorber which is solid at ordinary temperature, since it is desired that the ultraviolet absorber be in a fully dissolved state in the microcapsules, the amount of organic solvent, for example in case of microcapsules of polyurea resin or polyurethane resin, is adjusted generally from to usually 10 to 60 wt. %, or from to 20 to 60 wt. %, based on the combined amount of organic solvent, ultraviolet absorber and wall-forming material. Further, in case of microcapsules of aminoaldehyde resin, the amount of organic solvent is adjusted to usually 50 to 2000% by weight, generally from 100 to 1000% by weight of ultraviolet absorber.

Additionally, an absorber may be utilized. An absorber should be selected which reduces the sensitivity of the microcapsule in those portions of its spectral sensitivity range which interfere with the exposure of microcapsules at other wavelengths (its inactive range) without overly reducing the sensitivity of the microcapsule in those portions of the spectral sensitivity range in which the microcapsule is intended to be exposed (its active range). In some cases it may be necessary to balance the absorption characteristics of the absorber in the active range and the inactive range to achieve optimum exposure characteristics. Generally absorbers having an extinction coefficient greater than about 100/M cm in the inactive range and less than about 100,000/M cm in the active range of the microcapsule are used. When the absorber is directly incorporated into the photosensitive composition, ideally, it should not inhibit free radical polymerization, and it should not generate free radicals upon exposure.

The absorbers used in the present invention can be selected from among those absorbers which are known in the photographic art. Examples of such compounds include dyes conventionally used as silver halide sensitizing dyes in color photography (e.g., cyanine, merocyanine, hemicyanine and styryl dyes) and ultraviolet absorbers. A number of colored dyes which absorb outside the desired sensitivity range of the microcapsules and do not absorb heavily within the range could also be used as absorbers in the present invention. Among these, Sudan I, Sudan II, Sudan III, Sudan Orange G, Oil Red O, Oil Blue N, and Fast Garnet GBC are examples of potentially useful compounds.

Additionally ultraviolet absorbers that may be desirable include those selected from hydroxybenzophenones, hydroxyphenylbenzo-triazoles and formamidines. The absorbers may be used alone or in combination to achieve the spectral sensitivity characteristics that are desired.

Representative examples of useful hydroxybenzophenones are 2-hydroxy-4-n-octoxybenzophenone (UV-CHEK AM-300 from Ferro Chemical Division, Mark 1413 from Argus Chemical Division, Witco Chem. Corp., and Cyasorb UV-531 Light Absorber from American Cyanamid), 4-dodecyl-2-hydroxybenzophenone (Eastman Inhibitor DOBP from Eastman Kodak), 2-hydroxy-4-methoxybenzophenone (Cyasorb UV-9 Light Absorber from American Cyanamid), and 2,2'-dihydroxy-4-methoxybenzophenone (Cyasorb UV-24 Light Absorber from American Cyanamid). Representative examples of useful hydroxybenzophenyl benzotriazoles are 2-(2'-hydroxy-5'-methylphenyl)benzotriazole (Tinuvin P from Ciba-Geigy Additives Dept.), 2-(3',5'-di-tert-butyl-2'hydroxyphenyl)-5-chlorobenzotriazole (Tinuvin 327 from Ciba-Geigy), and 2-(2-hydroxy-5-t-octylphenyl)benzotriazole (Cyasorb UV-5411 Light Absorber from American Cyanamid). Representative examples of useful formamidines are described in U.S. Pat. No. 4,021,471 and include N-(p-ethoxy-carbonylphenyl)-N'-ethyl-N'-phenylformamidine (Givsorb UV-2 from Givaudan Corp.). The optimum absorber and concentration of absorber for a particular application depends on both the absorption maximum and extinction coefficient of the absorber candidates and the spectral sensitivity characteristics of the associated photoinitiators.

Additionally, the microcapsules, photosensitive compositions, image-forming agents, developers, and development techniques described in U.S. Pat. Nos. 4,399,209 and 4,440,846, the contents of which are incorporated and may be used in the present invention.

The compounds according to the present invention are also particularly effective against powdery mildews and rusts, pyrenophora, rhynchosporium, tapesia, fusarium and leptosphaeria fungi, in particular against pathogens of monocotyledonous plants such as cereals, including wheat and barley. They are furthermore particularly effective against downy mildew species, powdery mildews, leaf spot diseases and rusts in dicotyledonous plants.

The amount of the compounds of the invention to be applied, will depend on various factors such as the compound employed, the subject of the treatment (substrate), the type of treatment (e.g. spraying, dusting, seed dressing), the purpose of the treatment (prophylactic or therapeutic), the type of fungi and/or bacteria to be treated and the application time.

The agents may be applied before or after infection of any of the materials listed by the fungi and/or bacteria.

When applied to the plants the compound of formula I is applied at a rate of 25 to 250 g/ha, generally from 50 to 150 g/ha, e.g. 75, 100, 125 or 150 g/ha, in association with 20 to 2000 g/ha, generally from 20 to 1000 g/ha.

In industrial practice the application rates of the combination depend on the type of effect desired, and range from 0.02 to 3 kg of active ingredient per hectare.

When the active ingredients are used for treating seed, rates of 0.001 to 50 g a.i. per kg, and generally from 0.01 to 10 g per kg of seed are generally sufficient.

The composition of the invention can be employed in any conventional form, for example in the form of a twin pack, an instant granulate, a flowable formulation, an emulsion concentrate or a wettable powder in combination with industrially acceptable adjuvants, including surfactants such as sodium lauryl sulfate. Such compositions may be produced in conventional manner, e.g. by mixing the active ingredients with appropriate adjuvants (diluents or solvents and optionally other formulating ingredients such as surfactants). Also conventional slow release formulations may be employed where long lasting efficacy is intended.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% industrially acceptable surfactant and 10 to 99.99% solid or liquid adjuvant(s), the active agent consisting of at least the compound of formula I, and optionally other active agents, particularly microbides or conservatives or the like. Concentrated forms of compositions generally contain in between about 2 and 80%, generally from between about 5 and 70% by weight of active agent. Application forms of formulation may for example contain from 0.01 to 20% by weight, generally from 0.01 to 5% by weight of active agent. Whereas commercial products will generally be formulated as concentrates, the end user will normally employ dilute formulations.

Additionally, the color of the present compounds may be removed by a type of "bleaching". Furthermore, it has been found possible to bleach the colored substances leached from the present compound in dyed textiles and building materials or from textiles and building materials soiled with a colorant in a solution of wash liquor thereby preventing the colored substance in question from being deposited on other textiles and building materials in the wash liquor, when enzymes utilizing hydrogen peroxide or molecular oxygen for the oxidation of organic or inorganic substances, including colored substances, are added to the wash liquor. Such enzymes are usually termed peroxidases and oxidases, respectively. It is well recognized in the art (cf. for instance B. C. Saunders et al., Peroxidase, London, 1964, p. 10 ff.) that peroxidases act on various amino and phenolic compounds resulting in the production of a color. In view of this, it must be considered surprising that peroxidases (and certain oxidases) may also exert an effect on colored substances in solution such that dye transfer is inhibited. While the mechanism governing the ability of these enzymes to effect dye transfer inhibition has not yet been elucidated, it is currently believed that the enzymes act by reducing hydrogen peroxide or molecular oxygen and oxidizing the colored substance (donor substrate) dissolved or dispersed in the wash liquor, thereby either generating a colorless substance or providing a substance which is not adsorbed to the fabric or building material.

Additionally, a liquid composition of matter according to the present invention may be formed and may be mixed with and/or diluted by an excipient. When the excipient serves as a diluent, it may be a solid, semi-solid, or liquid material that acts as a vehicle, carrier, or medium for the composition of matter. Various suitable excipients will be understood by those skilled in the art and may be found in the *National Formulary*, 19: 2404-2406 (2000), the disclosure of pages 2404 to 2406 being incorporated by reference herein in their entirety. Preferable excipients include butanedioal and EDTA. Examples of suitable excipients include, but are not limited to, starches, gum arabic, calcium silicate, microcrystalline cellulose, methacrylates, shellac, polyvinylpyrrolidone, cellulose, water, syrup, and methylcellulose. An aqueous medium may include an active ingredient or ingredients, a quantity of one or more surfactants sufficient to dissolve or suspend said active ingredients uniformly throughout the medium and other manufacturing additives as known to the art. The latter include granulating-binding agents such as gelatin; natural gums, such as acacia, tragacanth; starches, sodium alginate, sugars, polyvinylpyrrolidone; cellulose derivatives such as hydroxypropylmethylcellulose, polyvinyloxoazolidones; pharmaceutical fillers such as lactose, microcrystalline cellulose, dicalcium phosphate, tricalcium phosphate, calcium sulfate, dextrose, mannitol, sucrose; tabletting lubricants if needed such as calcium and magnesium stearate, stearic acid, talc, sterotex (alkaline stearate). The term "aqueous medium" for one ingredient of one of the embodiments of the invention is used within the custom of the art. Primarily, it connotes a water medium, with added water-miscible solvents such as isopropanol or ethanol when needed, to support the active ingredient.

The present invention is explained in greater detail in the Examples that follow. These examples are intended as illustrative of the invention and are not to be taken are limiting thereof.

EXAMPLE 1

Synthesis of 1-Ethyl-(E,E)-2,6-bis[2-[4-(pyrrolidinyl)phenyl]ethenyl]pyridinium Chloride (6)

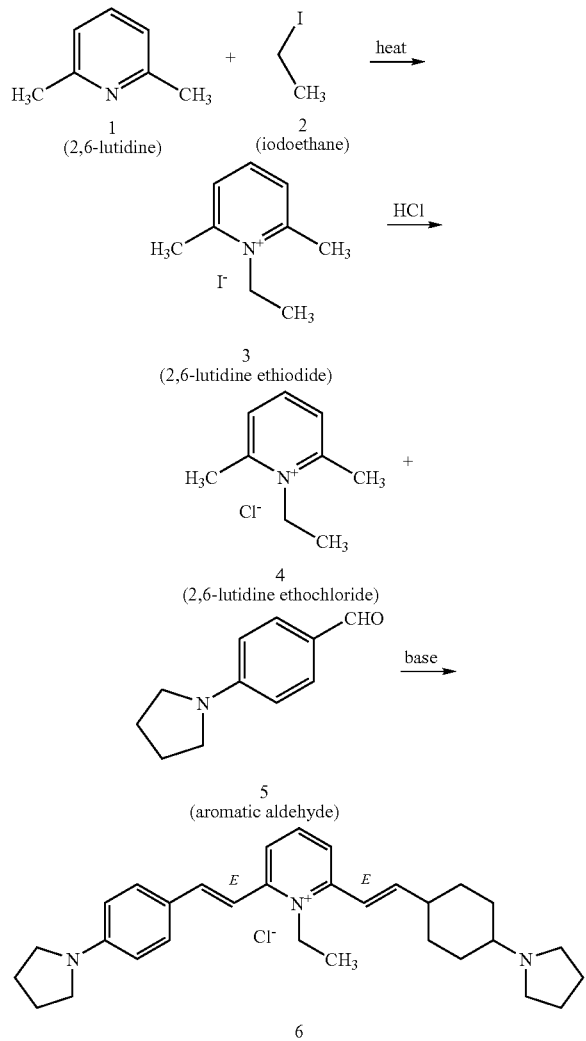

Step a: Reaction of 2,6-Lutidine (1) and Iodoethane (2) to Form 2,6-Lutidine Ethiodide (3). A total of 69.7 grams (0.65 mole) of 2,6-lutidine (1) was combined with 202.8 grams of ethyl iodide (2) and the mixture was heated at 100° C. overnight. The reaction mixture was then cooled and the precipitated 2,6-lutidine ethiodide (3) was collected by filtration. The filtrate was reheated to 100° C. overnight, then cooled and filtered to recover a second crop of solid 2,6-lutidine ethiodide (3). These two crops were combined, dissolved in hot absolute ethanol and recrystallized. This resultant solid was dissolved in hot ethanol and recrystallized a second time. The purified 2,6-lutidine ethiodide (3) was air dried to constant weight to yield 107.5 grams of desired product. The $^1$H-NMR was consistent with the desired material and the uncorrected melting point was determined to be 205-206° C.

Step b: Conversion of 2,6-Lutidine Ethiodide (3) to 2,6-Lutidine Ethochloride (4). The 107.5 grams of 2,6-lutidine ethiodide was dissolved in 2.0 liters of methanol and the solution was chilled in an ice-water bath. A total of 220 grams of anhydrous hydrogen chloride gas was slowly added to the solution via a gas bubbler. An ice-water bath was used to keep the reaction temperature below 30° C. during the hydrogen chloride addition. After all the hydrogen chloride had been added, the reaction mixture was stirred overnight at room temperature. The reaction mixture was concentrated to near dryness and then re-dissolved in 1.0 liter of methanol. A total of 103 grams of anhydrous hydrogen chloride gas was then bubbled into the mixture. After stirring for 10 minutes, the reaction mixture was concentrated to dryness under vacuum to yield 94.3 grams of the desired 2,6-lutidine ethochloride (4).

Step c: Reaction of 2,6-Lutidine Ethochloride (4) and 4-Pyrrolidinobenzaldehyde (5) to Produce 1-Ethyl-(E,E)-2,6-bis[2-[4-(pyrrolidinyl)phenyl]ethenyl]pyridinium Chloride (6). A mixture of 30.6 grams (0.22 mole) of 2,6-lutidine ethochloride (4), 75 grams (0.54 mole) of 4-pyrrolidinobenzaldehyde (5), 12 mL piperidine and ca. 2 liters of methanol was heated at reflux overnight. The $^1$H NMR indicated that no reaction had occurred. No reaction occurred after heating the reaction mixture for an additional 96 hours at reflux. An additional 12 mL of piperidine was added and heating at reflux continued. After a total of 120 hours of heating at reflux, some solids began precipitating but $^1$H NMR indicated that the desired reaction was still incomplete. Another 12 mL of piperidine catalyst was added and the reaction mixture was heated at reflux for an additional 24 hours. The $^1$H NMR spectrum now indicated the desired reaction was carried to completion. The reaction mixture was slowly cooled to room temperature and the precipitated solid containing 1-ethyl-(E,E)-2,6-bis[2-[4-(pyrrolidinyl)phenyl]ethenyl]pyridinium chloride (6) was collected by filtration. The solid was triturated and washed with three 100 ml portions of ethyl ether to remove impurities and residual methanol solvent. The solid was air dried and dried under vacuum to constant weight to yield 32.6 grams of red crystalline 1-ethyl-(E,E)-2,6-bis[2-[4-(pyrrolidinyl)phenyl]ethenyl]pyridinium chloride (6)—high performance liquid chromatography area percent (HPLC Area %)=98.1%, $^1$H NMR (DMSO, $d_6$); ppm 8.16-8.14 (t, 1H); 8.08-8.07 (d, 2H); 7.71-7.68 (d, 1H); 7.69-7.67 (d, 2H, J=8.8 Hz); 7.23-7.20 (d, 1H); 6.61-6.59 (d, 2H, J=8.8 Hz); 4.75-4.74 (m, 2H); 3.31 (m, 2H); 1.98-1.96 (m, 2H); 1.48-1.45 (t, 3H).

The reaction filtrate was concentrated to approximately one-half the original volume, 10 mL of piperidine was added and the dark reaction filtrate was heated at reflux for 24 hours. $^1$H NMR spectral analysis indicated that more 1-ethyl-(E,E)-2,6-bis[2-[4-(pyrrolidinyl)phenyl]ethenyl]pyridinium chloride (6) had formed, possibly by olefinic isomer equilibration. The heat was removed and the reaction mixture was allowed to stir at room temperature for 48 hours, during which time a precipitate formed. The solid was collected by filtration and was triturated and washed with three 100 ml portions of ethyl ether to remove impurities and residual methanol solvent. The red crystalline solid was air dried and dried under vacuum to constant weight to yield 19.2 grams of additional 1-ethyl-(E,E)-2,6-bis[2-[4-(pyrrolidinyl)phenyl]ethenyl]pyridinium chloride (6)—HPLC Area %=97.4%, $^1$H NMR was consistent with the first crop of product (6).

EXAMPLE 2

Synthesis of 1-Ethyl-(E,E)-2,6-bis[2-[4-(dimethylamino)phenyl]ethenyl]pyridinium Chloride

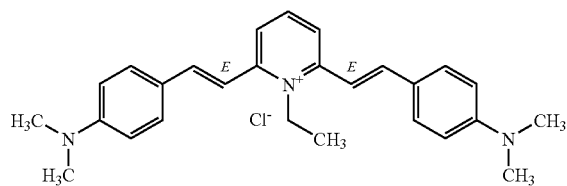

A mixture of 9.0 grams (0.07 mole) of 2,6-lutidine ethochloride, 23.6 grams (0.16 mole) of 4-dimethylaminobenzaldehyde, 14 mL piperidine and 350 mL methanol was heated at reflux for 77 hours. After 77 hr at reflux, high performance liquid chromatography—mass spectral analysis (LC/MS analysis) indicated that the desired product was present in the reaction mixture. The reaction mixture was slowly cooled to effect precipitation and the precipitated solids were collected by filtration. The solids were triturated and washed with three 100 ml portions of ethyl ether to remove impurities and residual methanol solvent. The solid was air dried and dried under vacuum to constant weight to yield 2.8 grams of red crystalline 1-ethyl-(E,E)-2,6-bis[2-[4-(dimethylamino)phenyl]ethenyl]pyridinium chloride—high performance liquid chromatography area percent (HPLC Area %)=99.5%, $^1$H NMR (DMSO, $d_6$) consistent with the desired product.

The reaction filtrate was concentrated to approximately one-half the original volume. A total of 10 mL of piperidine catalyst was added and the dark solution was heated at reflux for an additional 24 hours. At this point high performance liquid chromatography area percent analysis (HPLC A% analysis) indicated that more product had formed and the 2,6-lutidine ethochloride starting material was almost gone. The heat was removed and the reaction was concentrated under vacuum to yield a heavy slurry. The precipitated solid was collected by filtration, washed with three 100 ml portions of ethyl ether and the resulting solid was air dried and vacuum dried overnight to yield 13.6 grams of red crystalline 1-ethyl-(E,E)-2,6-bis[2-[4-(dimethylamino)phenyl]ethenyl]pyridinium chloride—HPLC Area %=99%, $^1$H NMR was consistent with the desired product.

EXAMPLE 3

Synthesis of 1-Ethyl-(E,E)-2,6-bis[2-[4-(diethylamino)phenyl]ethenyl]pyridinium Chloride

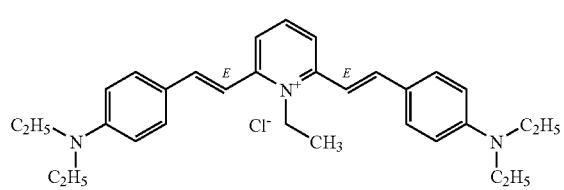

A mixture of 9.0 grams (0.07 mole) of 2,6-lutidine ethochloride, 28.1 grams (0.16 mole) of 4-diethylaminobenzaldehyde, 14 mL piperidine and 350 mL methanol was heated to reflux for 96 hours at which time LC/MS analysis indicated that the desired product was present. The reaction mixture was cooled and concentrated under vacuum to produce a slurry. The solid was collected by filtration and was triturated and washed with three 50 ml portions of ethyl ether. The resulting purified solid was air dried and vacuum dried to yield 17.3 grams of red crystalline 1-ethyl-(E,E)-2,6-bis[2-[4-(diethylamino)phenyl]ethenyl]pyridinium chloride—high performance liquid chromatography area percent (HPLC Area %)=95%, $^1$H NMR (DMSO, $d_6$) was consistent with the desired material and a trace of the starting 4-diethylaminobenzaldehyde present.

EXAMPLE 4

Synthesis of 1-Ethyl-(E,E)-2,6-bis[2-[4-(pyrrolidinyl)phenyl]ethenyl]pyridinium 4-Aminobenzoate Salt

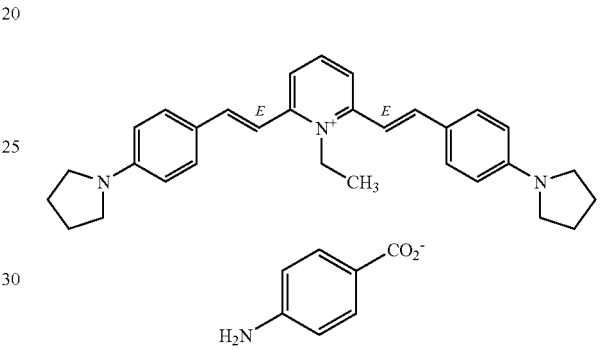

A total of 52.8 g (0.12 mole) of 1-ethyl-(E,E)-2,6-bis[2-[4-(pyrrolidinyl)phenyl]ethenyl]pyridinium chloride and 18.6 grams (0.12 mole) of the sodium salt of 4-aminobenzoic acid (sodium salt of p-aminobenzoic acid, Na$^+$ PABA$^-$) were dissolved in 1.3 liters of methanol and this mixture was allowed to stir at room temperature for 4 days during which time a precipitate formed. The reaction mixture was then filtered and the solid salt was air dried and vacuum dried to yield a first crop of 28.0 grams of 1-ethyl-(E,E)-2,6-bis[2-[4-(pyrrolidinyl)phenyl]ethenyl]pyridinium 4-aminobenzoate salt (also termed the PABA salt). The filtrate was concentrated under vacuum to produce more precipitate. Isolation of the second crop was effected by filtration followed by air drying and vacuum drying of the solid to afford a second crop of 42.6 grams of 1-ethyl-(E,E)-2,6-bis[2-[4-(pyrrolidinyl)phenyl]ethenyl]pyridinium 4-aminobenzoate salt (also termed the PABA salt)—high performance liquid chromatography area percent (HPLC A%) first crop=99.6% excluding PABA; HPLC A% second crop=99.9% excluding PABA; $^1$H NMR and Mass Spectral analyses for both crops were consistent with structure of the desired material 1-ethyl-(E,E)-2,6-bis[2-[4-(pyrrolidinyl)phenyl]ethenyl]pyridinium 4-aminobenzoate salt. This product is also named 1-ethyl-(E,E)-2,6-bis[2-[4-(pyrrolidinyl)phenyl]ethenyl]pyridinium p-aminobenzoate salt or 1-ethyl-(E,E)-2,6-bis[2-[4-(pyrrolidinyl)phenyl]ethenyl]pyridinium PABA salt.

By the methods demonstrated in Examples 1-3, substituted and unsubstituted aromatic aldehydes or substituted and unsubstituted heteroaromatic aldehydes are reacted with substituted and unsubstituted lutidine ethochloride salts, lutidine isobutochloride salts, lutidine methochloride salts, lutidine 1,1,1-trifluoroethochloride salts and the like and with secondary amine catalysts such as piperidine and pyrrolidine in polar protic solvents such as methanol, ethanol, 2-propanol and the like or polar aprotic solvents such as acetonitrile (ACN), dimethyl acetamide (DMA), dimethyl formamide (DMF), dimethyl sulfoxide (DMSO) and the like to yield any possible combination of compounds as noted throughout the application and the claims. Applicants have additionally provided numerous compounds shown in FIGS. 1-4 to illustrate some of the possible combinations of the present invention.

In the following Examples, the "active ingredient" may be any compound of formula (I) as recited above or a pharmaceutically acceptable salt or solvate thereof.

EXAMPLE 5

Antibacterial Activity

Solutions of formula I, stilbazium chloride, (1% dimethylsulfoxide) were diluted with sterile water, using serial half-step dilutions. Forty microliters of each dilution were then pipetted onto seeded Mueller-Hinton agar plates. The agar plates were then incubated for 24 hours at 35° C. and zones of inhibition were then recorded. The Minimum Inhibitory Concentration (MIC) was the lowest concentration of the test material which produced a zone of inhibition against the organism. The MIC for formula I against a series of organisms is listed in the table below.

TABLE 1

Anti-bacterial activity of formula I

| Strain | MIC |
| --- | --- |
| Streptococcus pyogenes | 1.0 |
| Streptococcus faecalis | 1.0 |
| Streptococcus algalactia | 1.0 |
| Staphylococcus aureus | 0.3 |
| Bordella bronchiseptica | 1.0 |
| Vibrio cholerae | 10.0 |
| Pasturella multocida | 3.0 |
| E. coli | >100 |
| Pseudomonas aerugenosa | >100 |

* The data represent the minimal inhibitory concentrations of formula I, in µg/mL, for inhibition of bacterial growth, cultured in vitro.

EXAMPLE 6

Antifungal Activity

Fungal strains (obtained from ATCC) were grown in Mueller-Hinton broth for 18 hours at 35° C. Plates were then seeded with the broth culture and allowed to air-dry at room temperature (22° C.) for about 10-15 minutes. Forty microliters of formula I (in 1% dimethylsulfoxide) and serial half-step dilutions in water were then pipetted onto the seeded Mueller-Hinton agar plates. The plates were then incubated for 24 hours at 35° C. and zones of inhibition were then recorded. The Minimum Inhibitory Concentration (MIC) was the lowest concentration of formula I which produced a zone of inhibition against the organism. The following table lists the antifungal activity of formula I against various fungal strains.

TABLE 2

Inhibition of yeast and fungal growth by Formula I in vitro

| Organism | MIC |
| --- | --- |
| Candida albicans | <0.006 |
| Candida tropicalis | <0.4 |
| Cryptococcus neoformans | <0.4 |
| Saccharomyces cervisciae | <0.4 |
| Aspergillus fumigatus | <0.006 |
| Aspergillus flavus | 6.25 |
| Fusarium solani | <0.4 |
| Rhizopus arrihizus | 6.25 |
| Microsporidium canis | 1.6 |
| Microsporidium gypseum | 1.6 |
| Trichophyton equinium | 1.6 |
| Trichophyton mentagrophyt | 1.6 |
| Trichophyton rubrum | 1.6 |
| Epidermophyton floccsum | 1.6 |

* The data represent the minimal inhibitory concentrations of formula I, in µg/mL, for inhibition of bacterial growth, cultured in vitro.

EXAMPLE 7

Stilbazium iodide was tested against a panel of plant relevant mold stains. A stock solution of the compound was prepared in DMSO at a concentration of 10,000 ppm a.i. Further dilutions were prepared with water. The test was conducted at the following concentrations: 125, 31, 8, 21, 0.5 and 0.125 ppm a.i. Spore suspensions of the fungi were prepared. The test was conducted in microtiter plates and for each fungus and each concentration, 3 wells were prepared. Incubation of the inoculated plates was carried out at 18° C. for 7 days. After this time, the optical density of the mycelium developed in each well was measured at 405 nm.

The data produced, shown in Table 3, allowed an assessment of the IC 90 value (the concentration at which the fungal growth was reduced by at least 90% compared to the control).

TABLE 3

| Organism | Plant Relevance | IC90 |
| --- | --- | --- |
| Alternaria solani | Potato | >125 |
| Botrytis cinerea | Vegetable | 0.5 |
| Cochliobolus mijabeanus | Corn | >125 |
| Colletotrichum lagenarium | Mellons | 31 |
| Fusarium culmorum | Wheat Head | >125 |
| Phytophthora infestans | Tomato | 2 |
| Pyrenophora teres | Barley | 31 |
| Pyricularia oryzae | Rice | 8 |
| Rhizoctonia solani | Rice Sheath | 2 |
| Septonia tritici | Wheat Leaf | 2 |

EXAMPLE 8

The data shown below in Table 4 illustrates various bacteria and fungi that can be treated by stilbazium compounds. The data illustrates the overall effectiveness of various stilbazium compounds.

TABLE 4

| Species | Isolate # | MIC 80% | MIC 100% | MFC |
| --- | --- | --- | --- | --- |
| Alternaria species | 128.89 | 6.25 | 12.5 | >100 |
| Aspergillus flavus | 112.96 | 3.12 | 6.25 | 6.25 |
| Aspergillus flavus | 194.99 | 3.12 | 3.12 | 12.5 |
| Aspergillus flavus | 107.96 | 6.25 | 12.5 | 25 |

TABLE 4-continued

| Species | Isolate # | MIC 80% | MIC 100% | MFC |
|---|---|---|---|---|
| Aspergillus flavus | 141.88 | 12.5 | 25 | 25 |
| Aspergillus flavus | 178.03 | 12.5 | 25 | >25 |
| Aspergillus flavus | 173.03 | 25 | 25 | >25 |
| Aspergillus fumigatus | 168.95 | 3.12 | 6.25 | >25 |
| QC A. fumigatus | 168.95 | 3.12 | 6.25 | >100 |
| QC A. fumigatus | 168.95 | 3.12 | 6.25 | >100 |
| Aspergillus fumigatus | 111.02 | 3.12 | 6.25 | 12.5 |
| Aspergillus fumigatus | 153.90 | 12.5 | 25 | 25 |
| Aspergillus fumigatus | 182.99 | 12.5 | 25 | >25 |
| Aspergillus sydowii | 165.02 | 0.78 | 1.56 | 3.12 |
| Aspergillus versicolor | 120.02 | 1.56 | 3.12 | 6.25 |
| Bipolaris spicifera | 155.89 | 3.12 | 3.12 | >100 |
| Candida albicans | A39 | 0.39 | 0.39 | 0.39 |
| Candida albicans | 117.00 | 0.39 | 0.39 | 0.39 |
| QC C. albicans | 117.00 | 1.56 | 1.56 | 3.12 |
| QC C. albicans | 117.00 | 3.12 | 3.12 | 6.25 |
| Candida albicans | 117.00 | 0.78 | 1.56 | 3.12 |
| Candida albicans | 116.98 | 0.39 | 0.39 | 1.56 |
| Candida albicans | 126.97 | 0.39 | 0.78 | 0.78 |
| Candida albicans | 149.97 | 0.39 | 0.39 | 0.78 |
| Candida albicans | 159.95 | 0.39 | 0.39 | 1.56 |
| Candida albicans | 156.97 | 1.56 | 1.56 | 1.56 |
| Candida albicans | 203.03 | 1.56 | 1.56 | 3.12 |
| Candida albicans | 204.03 | 1.56 | 1.56 | 1.56 |
| Candida albicans | 205.03 | 1.56 | 1.56 | 6.25 |
| Candida albicans | 206.03 | 3.12 | 3.12 | 12.5 |
| Candida albicans | 202.03 | 3.12 | 3.12 | 3.12 |
| Candida parapsilosis | 110.01 | 0.78 | 0.78 | 3.12 |
| Candida parapsilosis | ATCC 22019 | 0.78 | 0.78 | 3.12 |
| Candida parapsilosis | 109.96 | 1.56 | 1.56 | 3.12 |
| Candida parapsilosis | 118.02 | 1.56 | 1.56 | 6.25 |
| Candida parapsilosis | 123.00 | 1.56 | 1.56 | 6.25 |
| Chaetomium species | T 217 | 1.56 | 3.12 | >100 |
| Cryptococcus neoformans | H99 | 0.012 | 0.024 | 1.56 |
| Curvularia lunata | 141.90 | 1.56 | 3.12 | >100 |
| Curvularia lunata | 110.90 | 3.12 | 3.12 | >100 |
| Curvularia lunata v. aerie | 104.89 | 3.12 | 6.25 | >100 |
| Curvularia lunata | 146.90 | 6.25 | 6.25 | >100 |
| Penicillium aurantiogriseum | 135.02 | 6.25 | 12.5 | >100 |
| Penicillium chrysogenum | 119.02 | 0.78 | 0.78 | 12.5 |
| Rhizopus oryzae | 172.86 | 1.56 | 6.25 | >100 |
| Rhizopus oryzae | 182.88 | 3.12 | 6.25 | >100 |
| Rhizopus oryzae | 318.86 | 3.12 | 6.25 | >100 |
| Rhizopus oryzae | 117.89 | 6.25 | 6.25 | 12.5 |
| Rhizopus oryzae | 127.88 | 12.5 | 12.5 | >25 |
| Rhizopus oryzae | 181.88 | 12.5 | 12.5 | >25 |
| Rhodotorula mucilaginosa | 213.03 | 1.56 | 3.12 | 6.25 |
| Rhodotorula mucilaginosa | 207.03 | 3.12 | 3.12 | 3.12 |
| Rhodotorula mucilaginosa | 209.03 | 3.12 | 6.25 | 6.25 |
| Rhodotorula mucilaginosa | 210.03 | 3.12 | 3.12 | 3.12 |
| Rhodotorula mucilaginosa | 211.03 | 6.25 | 6.25 | 6.25 |

In the specification, there has been disclosed typical preferred embodiments of the invention and, although specific terms are employed, they are used in a generic and descriptive sense only and not for purposes of limitation of the scope of the invention being set forth in the following claims.

What is claimed is:

1. An encapsulated formulation comprising a compound having the formula:

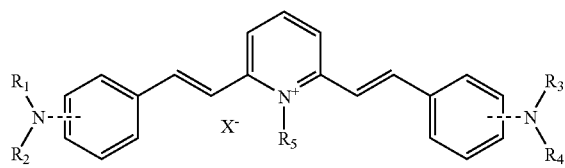

wherein the $NR_1R_2$ and $NR_3R_4$ moieties are in the ortho, meta or para position;
wherein $X^-$ is an anionic salt;
wherein $R_1$, $R_2$, $R_3$, or $R_4$ are independently selected from the group consisting of $C_{1-10}$ alkyl (linear or branched), alkenes (linear or branched), or wherein $R_1$ and $R_2$ or $R_3$ and $R_4$ taken together with the nitrogen atom to which they are attached form pyrrolidino or piperidino rings;
wherein $R_5$ is selected from the group consisting of $C_{1-10}$ alkyl (linear or branched), alkenes (linear or branched), alkynes, substituted and unsubstituted aryl moieties and substituted and unsubstituted benzyl moieties and the encapsulated formulation is a controlled-release formulation.

2. The encapsulated formulation of claim 1 further comprising an excipient and a photosensitive material.

3. The encapsulated formulation of claim 1 or 2, wherein the encapsulated formulation is a microcapsule.

4. The encapsulated formulation of claim 2, wherein the photosensitive material absorbs ultraviolet radiation.

5. The encapsulated formulation of claim 2, wherein the photosensitive material blocks ultraviolet radiation.

6. The microcapsule encapsulated formulation of claim 3, wherein the compound is (a) protected from oxidation and hydration, (b) released by melting, rupturing or biodegrading, (c) released by dissolving a surrounded shell matrix, and/or (d) released by slow diffusion of composition through the shell matrix.

7. An encapsulated formulation comprising a compound selected from the group consisting of 1-ethyl-(E,E)-2,6-bis[2-[4-(pyrrolidinyl)phenyl]ethenyl]pyridinium chloride, 1-ethyl-(E,E)-2,6-bis[2-[4-(dimethylamino)phenyl]ethenyl]pyridinium chloride, 1-ethyl-(E,E)-2,6-bis[2-[4-(diethylamino)phenyl]ethenyl]pyridinium chloride, 1-ethyl-(E,E)-2,6-bis[2-[4-(pyrrolidinyl)phenyl]ethenyl]pyridinium 4-aminobenzoate salt and 1-methyl-(E,E)-2,6-bis[2-[4-(pyrrolidinyl)phenyl]ethenyl]pyridinium chloride, wherein the compound is substantially free of any other configurational isomers.

8. The encapsulated formulation of claim 7 further comprising an excipient and a photosensitive material.

9. The encapsulated formulation of claim 7, wherein the encapsulated formulation is a microcapsule.

10. An encapsulated formulation comprising a compound having the formula:

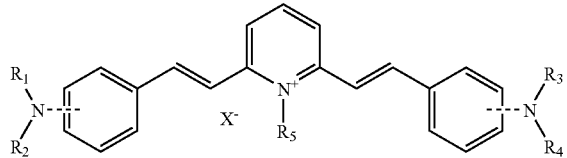

said compound is in an E, E configuration, and wherein
$NR_1R_2$ and $NR_3R_4$ are in the ortho, meta or para position;
$X^-$ is an anion;
$R_1$, $R_2$, $R_3$, or $R_4$ are independently selected from the group consisting of $C_{1-10}$ alkyl (linear or branched), alkenes (linear or branched), or wherein $R_1$ and $R_2$ or $R_3$ and $R_4$ taken together with the nitrogen atom to which they are attached form pyrrolidino or piperidino rings; and
$R_5$ is $(CH_2)_n$-$MR_6$, wherein n is a number from 1 to 6, M is an organometallic compound selected from the group consisting of tin, silicon, and germanium, and wherein $R_6$ is alkyl, substituted or unsubstituted.

11. The compound of claim 10, wherein $X^{31}$ is selected from the group consisting of fluoride, chloride, bromide, iodide halide, mesylate, tosylate, napthylate, nosylate, para-aminobenzoate, lauryl sulfate, 2,4-dihydroxy benzophenone, 2-(2-hydroxy-5'-methylphenyl) benzotriazole, benzenesulfonate, besylate, ethyl 2-cyano-3,3-diphenyl acrylate and 5-butyl phenyl salicylate.

12. The encapsulated formulation of claim 10, wherein M is silicon.

13. The encapsulated formulation claim 10, further comprising an excipient and a photosensitive material.

14. The encapsulated formulation of claim 10 or 13, wherein the encapsulated formulation is a microcapsule.

15. The encapsulated formulation of claim 13, wherein the photosensitive material absorbs ultraviolet radiation.

16. The encapsulated formulation of claim 13, wherein the photosensitive material blocks ultraviolet radiation.

17. The encapsulated formulation of claim 15, wherein the compound is (a) protected from oxidation and hydration, (b) released by melting, rupturing or biodegrading, (c) released by dissolving a surrounded shell matrix, and/or (d) released by slow diffusion of composition through the shell matrix.

18. A microcapsule comprising:
a compound selected from the group consisting of 1-ethyl-(E,E)-2,6-bis[2-[4-pyrrolidinyl)phenyl]ethenyl]pyridinium chloride, 1-ethyl-(E,E)-2,6-bis[2-[4-(dimethylamino)phenyl]ethenyl]pyridinium chloride, 1-ethyl-(E,E)-2,6-bis[2-[4-(diethylamino)phenyl]ethenyl] pyridinium chloride, 1-ethyl-(E,E)-2,6-bis[2-[4-(pyrrolidinyl)phenyl]ethenyl]pyridinium 4-aminobenzoate salt and 1-methyl-(E,E)-2,6-bis[2-[4-(pyrrolidinyl)phenyl]ethenyl]pyridinium chloride, wherein the compound is substantially free of any other configurational isomers; and
an excipient and a photosensitive material, wherein a ratio of the photosensitive material to the compound is 1:10.

19. A composition comprising the encapsulated formulation of claim 1.

20. A composition comprising the encapsulated formulation of claim 3.

21. A composition comprising the encapsulated formulation of claim 7.

22. A composition comprising the encapsulated formulation of claim 9.

23. A composition comprising the encapsulated formulation of claim 10.

24. A composition comprising the encapsulated formulation of claim 14.

25. A composition comprising a microcapsule of claim 15.

26. A method of combating fungi and/or bacteria in wood, air duct, paint, sheetrock, food packaging, or food products, wherein said method comprises administering to said wood, air duct, paint, sheetrock, food packaging, or food product an effective amount of a compound comprising:

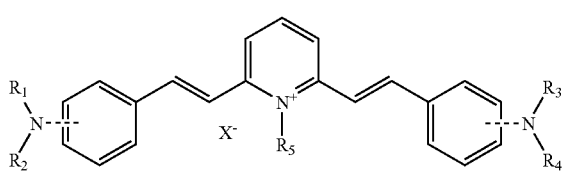

wherein the $NR_1R_2$ and $NR_3R_4$ moieties are in the ortho, meta or para position;
wherein $X^{31}$ is an anionic salt;

wherein $R_1$, $R_2$, $R_3$, or $R_4$ are independently selected from the group consisting of $C_{1-10}$ alkyl (linear or branched), alkenes (linear or branched), or wherein $R_1$ and $R_2$ or $R_3$ and $R_4$ taken together with the nitrogen atom to which they are attached form pyrrolidino or piperidino rings; and wherein $R_5$ is selected from the group consisting of $C_{1-10}$ alkyl (linear or branched), alkenes (linear or branched), alkynes, substituted and unsubstituted aryl moieties and substituted and unsubstituted benzyl moieties, and
wherein the compound is encapsulated.

27. The method of claim 26, wherein the compound is encapsulated in a microcapsule.

28. A method for treating an industrial product with fungal growth that comprises administering to the site where growth is to be treated an effective amount of a compound comprising:

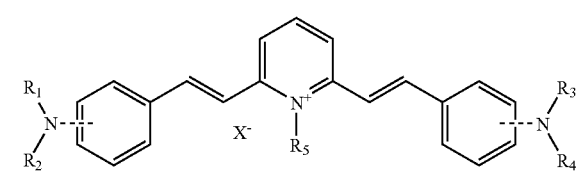

wherein the $NR_1R_2$ and $NR_3R_4$ moieties are in the ortho, meta or para position;
wherein $X^{31}$ is an anionic salt;
wherein $R_1$, $R_2$, $R_3$, or $R_4$ are independently selected from the group consisting of $C_{1-10}$ alkyl (linear or branched), alkenes (linear or branched), or wherein $R_1$ and $R_2$ or $R_3$ and $R_4$ taken together with the nitrogen atom to which they are attached form pyrrolidino or piperidino rings; and wherein $R_5$ is selected from the group consisting of $C_{1-10}$ alkyl (linear or branched), alkenes (linear or branched), alkynes, substituted and unsubstituted aryl moieties and substituted and unsubstituted benzyl moieties, and
wherein the compound is encapsulated.

29. The method of claim 28, wherein the compound is encapsulated in a microcapsule.

30. A method for treating an industrial product with fungal growth that comprises administering to the site where growth is to be treated an effective amount of a compound comprising:

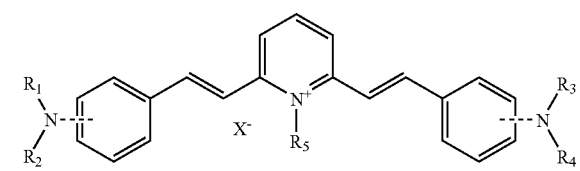

said compound is in an E, E configuration, and wherein
$NR_1R_2$ and $NR_3R_4$ are in the ortho, meta or para position;
$X^-$ is an anion;
$R_1$, $R_2$, $R_3$, or $R_4$ are independently selected from the group consisting of $C_{mo}$alkyl (linear or branched), alkenes (linear or branched), or wherein $R_1$ and $R_2$ or $R_3$ and $R_4$ taken together with the nitrogen atom to which they are attached form pyrrolidino or piperidino rings; and
$R_5$ is $(CH_2)_n$-$MR_6$, wherein n is a number from 1 to 6, M is an organometallic compound selected from the group consisting of tin, silicon, and germanium, and wherein R$_6$ is alkyl, substituted or unsubstituted, and wherein the compound is encapsulated.

31. The method of claim 30, wherein M is silicon.

32. The method of claim 30, wherein the compound is encapsulated in a microcapsule.

33. A method of controlling fungi and/or bacteria comprising administering a composition comprising:

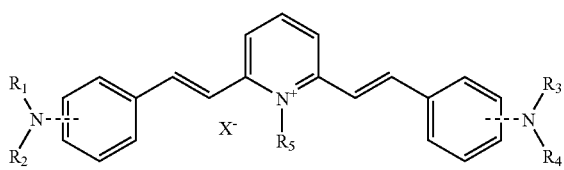

wherein the NR$_1$R$_2$ and NR$_3$R$_4$ moieties are in the ortho, meta or para position;

wherein X" is an anionic salt;

wherein R$_1$, R$_2$, R$_3$, or R$_4$ are independently selected from the group consisting of C$_{1-10}$ alkyl (linear or branched), alkenes (linear or branched), or wherein R$_1$ and R$_2$ or R$_3$ and R$_4$ taken together with the nitrogen atom to which they are attached form pyrrolidino or piperidino rings; and wherein R$_5$ is selected from the group consisting of methyl, ethyl, C$_{1-10}$ alkyl (linear or branched), alkenes (linear or branched), alkynes, substituted and unsubstituted aryl moieties and substituted and unsubstituted benzyl moieties, and wherein the compound is encapsulated.

34. A method of controlling fungi and/or bacteria comprising administering a composition comprising:

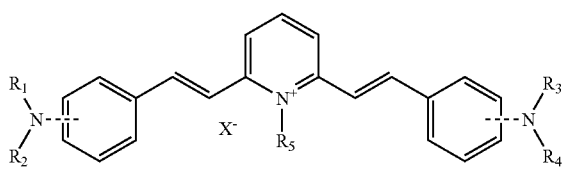

said compound is in an E, E configuration, and wherein

NR$_1$R$_2$ and NR$_3$R$_4$ are in the ortho, meta or para position;

X$^-$ is an anion;

R$_1$, R$_2$, R$_3$, or R$_4$ are independently selected from the group consisting of C$_{1-10}$ alkyl (linear or branched), alkenes (linear or branched), or wherein R$_1$ and R$_2$ or R$_3$ and R$_4$ taken together with the nitrogen atom to which they are attached form pyrrolidino or piperidino rings; and R$_5$ is (CH$_2$)$_n$-MR$_6$, wherein n is a number from 1 to 6, M is an organometallic compound selected from the group consisting of tin, silicon, and germanium, and wherein R$_6$ is alkyl, substituted or unsubstituted, and wherein the compound is encapsulated.

35. The method of claim 34, wherein M is silicon.

36. The method of claim 33 or 34, wherein the compound is encapsulated in a microcapsule.

37. The method of claim 33 or 34, wherein said method of controlling fungi and/or bacteria further comprises binding and containing the fungi and/or bacteria in the same area.

38. The method of claim 33 or 34, wherein said compound is administered before fungal growth occurs.

39. The method of claim 33 or 34, wherein said composition is administered to a substrate.

40. The method of claim 39, wherein said substrate is selected from the group consisting of sheetrock, lumber, decking, flooring, roofing, carpets, wallpaper, paneling, cloth caulking, mortar, tiles, grout, fasteners, adhesives, paint, coatings, sealants and stucco.

41. The method of claim 33 or 34, wherein said method further comprises administering said composition to a food packaging system to control fungi and/or bacteria by reducing fungal and/or bacterial growth.

42. The method of claim 33 or 34, wherein said method further comprises administering said composition to a medicinal product to control fungi and/or bacteria by reducing fungal and/or bacterial growth.

43. The method of claim 41, wherein said food packaging system is selected from the group consisting of plastic, paper and foam.

44. A method of controlling insects comprising administering an effective amount of a compound comprising:

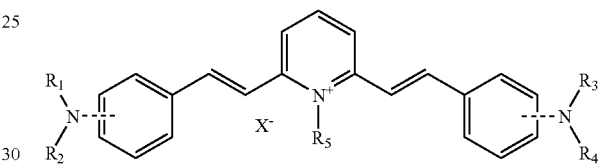

wherein the NR$_1$R$_2$ and NR$_3$R$_4$ moieties are in the ortho, meta or para position;

wherein X$^-$ is an anionic salt;

wherein R$_1$, R$_2$, R$_3$, or R$_4$ are independently selected from the group consisting of C$_{1-10}$ alkyl (linear or branched), alkenes (linear or branched), or wherein R$_1$ and R$_2$ or R$_3$ and R$_4$ taken together with the nitrogen atom to which they are attached form pyrrolidino or piperidino rings; and wherein R$_5$ is selected from the group consisting of C$_{1-10}$ alkyl (linear or branched), alkenes (linear or branched), alkynes, substituted and unsubstituted aryl moieties and substituted and unsubstituted benzyl moieties, and wherein the compound is encapsulated.

45. The method of claim 44, wherein the compound is encapsulated in a microcapsule.

46. A method of controlling insects comprising administering an effective amount of a compound comprising:

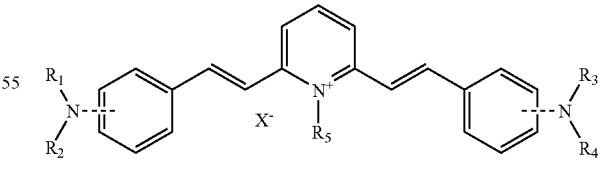

said compound is in an E, E configuration, and wherein

NR$_1$R$_2$ and NR$_3$R$_4$ are in the ortho, meta or para position;

X" is an anion;

R$_1$, R$_2$, R$_3$, or R$_4$ are independently selected from the group consisting of C$_{1-10}$ alkyl (linear or branched), alkenes (linear or branched), or wherein R$_1$ and R$_2$ or R$_3$ and R$_4$ taken together with the nitrogen atom to which they are attached form pyrrolidino or piperidino rings; and $R_5$ is $(CH_2)_n$-$MR_6$, wherein n is a number from 1 to 6, M is an organometallic compound selected from the group consisting of tin, silicon, and germanium, and wherein $R_6$ is alkyl, substituted or unsubstituted, and wherein the compound is encapsulated.

47. The method of claim 46, wherein M is silicon.

48. The method of claim 46, wherein the compound is encapsulated in a microcapsule.

* * * * *

UNITED STATES PATENT AND TRADEMARK OFFICE
CERTIFICATE OF CORRECTION

| | | |
|---|---|---|
| PATENT NO. | : 7,820,696 B2 | Page 1 of 1 |
| APPLICATION NO. | : 11/745111 | |
| DATED | : October 26, 2010 | |
| INVENTOR(S) | : Klein et al. | |

It is certified that error appears in the above-identified patent and that said Letters Patent is hereby corrected as shown below:

Column 17, Compound 6, Lines 46-49: correct

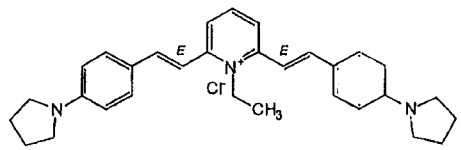

to read

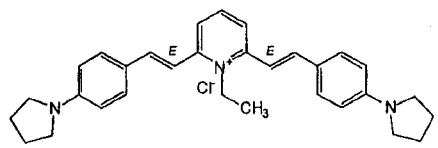

Column 24, Claim 6, Line 23: correct "The microcapsule encapsulated" to read -- The encapsulated --

Column 25, Claim 11, Line 1: correct "$X^{31}$" to read -- $X^-$ --
        Claim 17, Line 18: correct "claim 15" to read -- claim 14 --
        Claim 25, Line 49: correct "claim 15" to read -- claim 18 --
        Claim 26, Line 67: correct "$X^{31}$" to read -- $X^-$ --

Column 26, Claim 28, Line 30: correct "$X^{31}$" to read -- $X^-$ --
        Claim 30, Line 62: correct "$C_{mo}$" to read -- $C_{1-10}$ --

Column 27, Claim 33, Line 22: correct "X'"'" to read -- $X^-$ --

Column 28, Claim 46, Line 62: correct "X'"'" to read -- $X^-$ --

Signed and Sealed this
Seventeenth Day of May, 2011

David J. Kappos
*Director of the United States Patent and Trademark Office*